(12) United States Patent
Fonagy et al.

(10) Patent No.: US 8,722,863 B2
(45) Date of Patent: May 13, 2014

(54) SOLID STATE FORMS OF FIDAXOMYCIN AND PROCESSES FOR PREPARATION THEREOF

(71) Applicant: Teva Pharmaceutical Works Ltd., Debrecen (HU)

(72) Inventors: Tamas Fonagy, Monostorpalyi (HU); Adrienne Kovacsne-Mezei, Debrecen (HU); Levente Szuros, Ajak (HU); Edit Nagyne Arvai, Debresen (HU)

(73) Assignee: Teva Pharmaceutical Works Ltd., Debrecen (HU)

(*) Notice: Subject to any disclaimer, the term of this patent is extended or adjusted under 35 U.S.C. 154(b) by 0 days.

(21) Appl. No.: 13/896,711

(22) Filed: May 17, 2013

(65) Prior Publication Data

US 2013/0303472 A1     Nov. 14, 2013

Related U.S. Application Data

(63) Continuation of application No. PCT/US2013/040541, filed on May 10, 2013.

(60) Provisional application No. 61/645,214, filed on May 10, 2012, provisional application No. 61/662,542, filed on Jun. 21, 2012, provisional application No. 61/693,445, filed on Aug. 27, 2012, provisional application No. 61/718,286, filed on Oct. 25, 2012.

(51) Int. Cl.
*C07H 17/08*      (2006.01)
*A61K 31/7048*      (2006.01)

(52) U.S. Cl.
CPC ............ *C07H 17/08* (2013.01); *A61K 31/7048* (2013.01)
USPC .......................................... 536/17.1; 514/28

(58) Field of Classification Search
None
See application file for complete search history.

(56) References Cited

U.S. PATENT DOCUMENTS

| | | | |
|---|---|---|---|
| 3,978,211 | A | 8/1976 | Coronelli et al. |
| 7,378,508 | B2 | 5/2008 | Chiu et al. |
| 2013/0266986 | A1 | 10/2013 | Malcangi et al. |
| 2013/0267692 | A1 | 10/2013 | Fonte et al. |

FOREIGN PATENT DOCUMENTS

| | | |
|---|---|---|
| DE | 24 55 230 A1 | 5/1975 |
| EP | 2125850 | 12/2009 |
| WO | WO 2006/085838 A1 | 8/2006 |

OTHER PUBLICATIONS

J.E. Hochlowski et al., Tiacuminins, A Novel Complex of 18-Membered Macrolides, The Journal of Antibiotics, vol. XL, No. 5, May 1987, pp. 575-588.
Arnone, A. et al., "Structure Elucidation of the Macrocyclic Antibiotic Lipiarmycin", Journal of the Chemical Society, Perkin Transactions 1, Chemical Society, Letchworth; GB, Jan. 1, 1987, pp. 1353-1359.
Caira, M.R., "Crystalline Polymorphism of Organic Compounds", Topics in Current Chemistry, Springer, Berlin, DE, vol. 198, Jan. 1, 1998, pp. 163-208.

*Primary Examiner* — Eric S Olson
(74) *Attorney, Agent, or Firm* — Baker & Hostetler LLP

(57) ABSTRACT

The present invention provides solid state forms of Fidaxomycin, processes for preparing the solid state forms, as well as pharmaceutical compositions and formulations comprising one or more of the solid state forms of Fidaxomycin, and processes for the preparation of the compositions and formulations. The solid state forms of the present invention exhibit advantageous properties such as improved reliability and reproducibility in manufacturing and processing and stability in formulations.

23 Claims, 13 Drawing Sheets

SOLID STATE FORMS OF FIDAXOMYCIN AND PROCESSES FOR PREPARATION THEREOF

CROSS REFERENCE TO RELATED APPLICATIONS

This application is a continuation of PCT Application No. PCT/US13/40541, which claims the benefit of U.S. Provisional Application Nos. 61/645,214, filed May 10, 2012; 61/662,542, filed Jun. 21, 2012; 61/693,445, filed Aug. 27, 2012; and 61/718,286 filed Oct. 25, 2012, the contents of which are incorporated herein by reference.

FIELD OF THE INVENTION

The present invention relates to solid state forms of Fidaxomycin, processes for preparing the solid state forms and formulations comprising one or more of the solid state forms.

BACKGROUND OF THE INVENTION

Fidaxomycin, 3-(((6-Deoxy-4-O-(3,5-dichloro-2-ethyl-4,6-dihydroxybenzoyl)-2-O-methyl-β-D-mannopyranosyl)oxy)-methyl)-12(R)-[(6-deoxy-5-C-methyl-4-O-(2-methyl-1-oxopropyl)-b-D-lyxo-hexopyranosyl)oxy]-11(S)-ethyl-8(S)-hydroxy-18(S)-(1(R)-hydroxyethyl)-9,13,15-trimethyloxacyclooctadeca-3,5,9,13,15-pentaene-2-one, (IUPAC), has the following chemical structure:

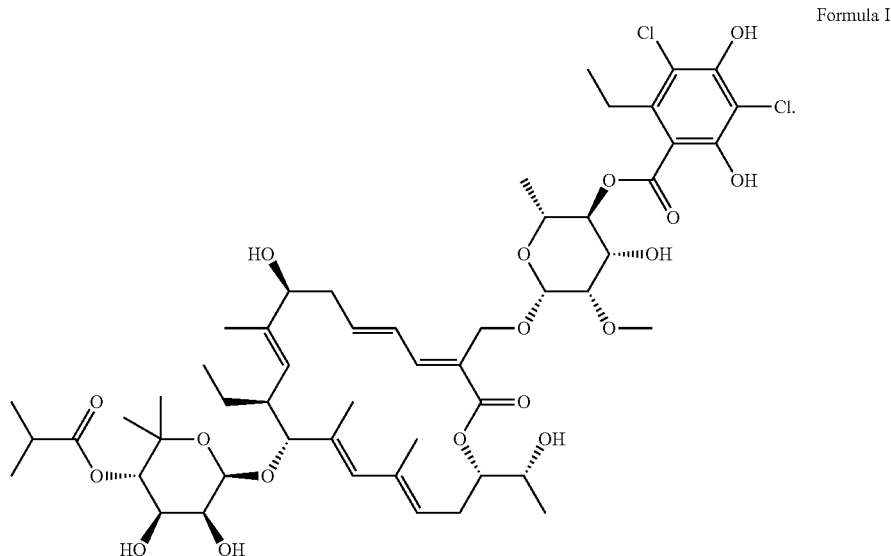 [SMILES: CCc1c(Cl)c(O)c(Cl)c(O)c1C(=O)O[C@H]1[C@H](O)[C@H](OC)[C@H](OC/C2=C\C=C\C[C@H](O)/C(C)=C/[C@H](CC)[C@@H](O[C@@H]3OC(C)(C)[C@@H](OC(=O)C(C)C)[C@H](O)[C@@H]3O)/C(C)=C/C(C)=C/C[C@@H]([C@@H](C)O)OC2=O)O[C@@H]1C]

Formula I

Fidaxomycin, formerly known as OPT 80, PAR 01, PAR 101, R-Tiacumicin B, Tiacumicin B, Lipiarmicin, Lipiarmycin, and Lipiarmycin A3, is a naturally occurring 18-membered macrocycle, which is derived from the fermentation of *Dactylosporangium aurantiacum* subspecies *hamdenesis*.

Fidaxomycin is being developed by Optimer Pharmaceuticals as an oral, narrow-spectrum antibacterial. In particular, Fidaxomycin shows activity against *Clostridium difficile*.

Fidaxomycin, and a process for its preparation, is disclosed in *Journal of Antibiotics*, vol. XL, no. 5, pages 575-588 (1987). Several solid state forms of mixtures containing Fidaxomycin as well as other tiacumicins are disclosed in U.S. Pat. No. 7,378,508 and its European counterpart EP 2 125 850 B1. In particular, two polymorphic forms termed form A and form B of "Fidaxomycin" (containing varying amounts of structural analogs) are described, and the applicant stated during prosecution that the claimed hydrated form A exhibits different thermodynamic properties and is more stable compared to the ethyl acetate solvate form B. The solid state forms of Fidaxomycin described therein were prepared by a procedure which required about 3 to about 14 days. In any event, the polymorphic forms described in these patents are comprised of mixtures of Fidaxomycin with up to 15% or more of other, structurally related tiacumicins.

Polymorphism, the occurrence of different crystal forms, is a property of some molecules and molecular complexes. A single molecule, like Fidaxomycin, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, and solid state NMR spectrum. One or more of these techniques may be used to distinguish different polymorphic forms of a compound.

Different solid state forms (including solvated forms) of an active pharmaceutical ingredient may possess different properties. Such variations in the properties of different solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different solid state forms may also offer improvements to the final dosage form, for instance, if they serve to improve bioavailability. Different solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new polymorphic forms and solvates of a pharmaceutical product can provide materials having desirable processing properties, such as ease of handling, ease of processing, low hygroscopicity, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., different crystal habits, higher crystallinity or polymorphic stability which may offer better processing or handling characteristics, improved dissolution profile, or improved shelf-life. Lastly, new polymorphic forms may be prepared with improved reliability and reproducibility in manufacturing and processing compared to other forms, for example, in terms of crystallinity or polymorphic purity.

SUMMARY OF THE INVENTION

The present invention provides solid state forms of Fidaxomycin, processes for preparing the solid state forms, pharmaceutical compositions and formulations comprising one or more of the solid state forms of Fidaxomycin, and a process for the preparation thereof.

The present invention also provides a method for the treatment of *Clostridium difficile* infection, or CDI, also known as *Clostridium difficile*-associated disease, or CDAD, comprising administering a therapeutically effective amount of one or more of the solid state forms of Fidaxomycin of the present invention, or a therapeutically effective amount of a pharmaceutical composition comprising one or more of the solid state forms of Fidaxomycin of the present invention, and optionally at least one pharmaceutically acceptable excipient to a patient in need thereof.

The present invention also provides the use of said solid state forms of Fidaxomycin in the manufacture of pharmaceutical compositions and formulations. The present invention thus further provides a pharmaceutical composition comprising one or more of the solid state forms of Fidaxomycin of the present invention. This pharmaceutical composition may additionally comprise at least one pharmaceutically acceptable excipient, thereby forming a pharmaceutical formulation that can, for example, be administered to patients in need of such treatment.

The present invention comprises a process for preparing the above-mentioned pharmaceutical formulations. The process comprises combining one or more of the solid state forms of Fidaxomycin of the present invention or a pharmaceutical composition comprising said one or more solid state forms of Fidaxomycin with at least one pharmaceutically acceptable excipient.

The solid state forms as defined herein as well as the pharmaceutical compositions and formulations of Fidaxomycin can be used as medicaments, particularly for the treatment of *Clostridium difficile* infection, or CDI, also known as *Clostridium difficile*-associated disease, or CDAD.

The present invention also provides the use of the solid state forms of Fidaxomycin, or at least one of the above pharmaceutical compositions or formulations of the present invention in the manufacture of a medicament for treating *Clostridium difficile* infection, or CDI, also known as *Clostridium difficile*-associated disease, or CDAD.

DETAILED DESCRIPTION OF THE INVENTION

Figure 1:
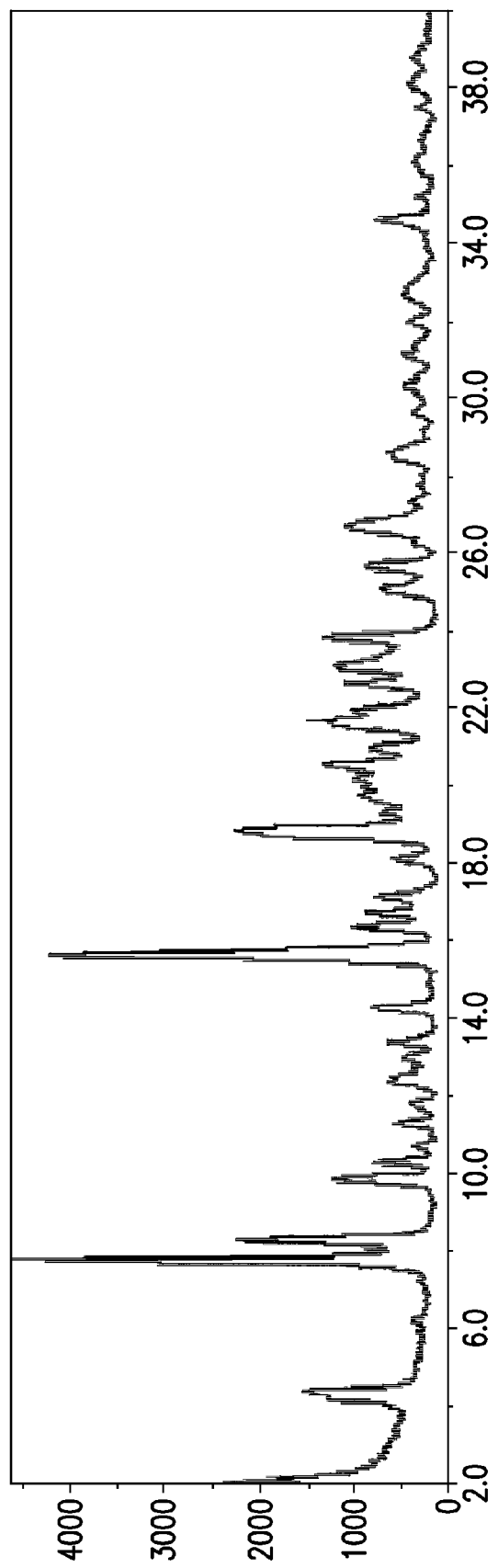
FIG. 1 shows a typical PXRD pattern for crystalline Fidaxomycin form Z (modification acetone).

The present invention provides solid state forms of Fidaxomycin, processes for preparing the solid state forms and formulations comprising one or more of the solid state forms, and a process for the preparation thereof.

The known solid state forms of Fidaxomycin, termed as form A and form B, are described as mixtures containing Fidaxomycin as well as up to 15% or more of a mixture of other, structurally related tiacumicins. The present invention provides solid state forms of Fidaxomycin which are not only polymorphically pure but also chemically pure.

Depending on which other solid state form they are compared with, the solid state forms of the present invention may have advantageous properties selected from at least one of: chemical or polymorphic purity, increased crystallinity, solubility, dissolution rate, bioavailability, morphology or crystal habit, specific surface and pycnometric density, stability— such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, flowability and bulk/tap density.

Solid state forms of Fidaxomycin comprise crystal forms, or crystalline forms, of Fidaxomycin. As used herein, solid state forms, crystal forms, crystalline forms, polymorphs and polymorphic forms are used interchangeably.

A crystal form may be referred to herein as being characterized by graphical data "substantially as depicted in" a Figure. Such data includes, for example, powder X-ray diffractograms and solid state NMR spectra. The graphical data potentially provides additional technical information to further define the respective solid state form which can not necessarily or easily be described by reference to numerical values for peak positions and/or relative intensities. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein, unless stated otherwise, the XRPD measurements are taken using copper $K_\alpha$ radiation wavelength 1.5406 Å.

As used herein, the expression "chemical shift difference" refers to the difference in chemical shifts between a reference signal and another signal in the same NMR spectrum. These chemical shift differences serve to provide an additional analytical measurement for a substance, for example a Fidaxomycin crystal form of the present invention, which will compensate for a phenomenon that may occur in NMR spectroscopy wherein a shift in the solid-state NMR "fingerprint" is observed. Such a shift in the NMR peaks may occur, for example as a result of variations in the instrumentation, the temperature, or the calibration method used in the NMR analysis. This shift in the solid-state NMR "fingerprint", having chemical shift resonances at a certain positions, is such that even though the individual chemical shifts of signals have moved, all the peaks in the spectrum are moved be the same amount, such that the difference between chemical shifts of each signal and another is retained. Thus, this shift may be used as a reliable characterization of the material being analyzed.

In the present patent application the chemical shift differences were calculated by subtracting the chemical shift value of the signal exhibiting the lowest chemical shift (reference signal) in the solid state $^{13}C$ NMR spectrum in the range of 100 to 180 ppm from chemical shift value of another (observed) signal in the same $^{13}CNMR$ spectrum in the range of 0 to 180 ppm.

A solid state form may be referred to herein as being characterized by data selected from two or more different data groupings, for example, by a powder XRD pattern having a group of specific peaks; or by a powder XRD pattern as shown in a figure depicting a diffractogram, or by "a combination thereof" (or by "combinations thereof," or by "any combination thereof," or by "combinations of these data"). These expressions, e.g., "any combination thereof" contemplate that the skilled person may characterize a crystal form using any combination of the recited characteristic analytical data. For example, the skilled person may characterize a crystal form using a group of, for example, four or five characteristic powder XRD peaks, and supplement that characterization with one or more additional features observed in the powder X-ray diffractogram, for example, an additional peak, a characteristic peak shape, a peak intensity, or even the absence of a peak at some position in the powder XRD pattern. Alternatively, the skilled person may, in some instances, characterize a crystal form using a group of, for example, four or five characteristic powder XRD peaks, and supplement that characterizing data with one or more additional features observed using another analytical method, for example, using one or more characteristic peaks in a solid state NMR spectrum, or characteristics of the DSC thermogram of the crystal form that is being characterized.

A crystal form (or polymorph) may be referred to herein as pure, highly pure or substantially free of any other crystalline (or polymorphic) forms. As used herein in this context, the expression "substantially free of any other forms" will be understood to mean that the crystalline form contains 20% or less, 10% or less, 5% or less, 2% or less, or 1% or less of any other forms of the subject compound as measured, for example, by PXRD. Thus, polymorphs of Fidaxomycin described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Fidaxomycin. Accordingly, in some embodiments of the invention, the described polymorphs of Fidaxomycin may contain from 1% to 20% (w/w), from 5% to 20% (w/w), or from 5% to 10% (w/w) of one or more other crystal forms of Fidaxomycin.

As used herein, the expression "room temperature" refers to a temperature between about 20° C. and about 30° C. Usually, room temperature ranges from about 20° C. to about 25° C.

As used herein, the term "overnight" refers to a period of between about 15 and about 20 hours, typically between about 16 to about 20 hours.

As used herein, the expression "wet crystalline form" refers to a polymorph that was not dried using any conventional techniques to remove residual solvent. Such conventional techniques include, but are not limited to, evaporation, vacuum drying, oven drying, drying under nitrogen flow, etc.

As used herein, the expression "dry crystalline form" refers to a polymorph that was dried using any conventional techniques to remove residual solvent. Such conventional techniques include, but are not limited to, evaporation, vacuum drying, oven drying, drying under nitrogen flow, etc.

As used herein, and unless stated otherwise, the term "anhydrous" in relation to crystalline Fidaxomycin relates to a crystalline Fidaxomycin which contains not more than 1% (w/w) of either water or organic solvents as measured by TGA. An anhydrous form of the solid states of Fidaxomycin of the present invention refers to a form that does not contain crystal water (or other solvents) in a defined, stoichiometric amount within the crystal.

As used herein and unless indicated otherwise, the term "non-hygroscopic" in relation to crystalline Fidaxomycin refers to less than 0.5%, and preferably less than 0.2% (w/w) absorption of water, for example atmospheric water, by the crystalline Fidaxomycin, as determined according to Ph. Eur. chapter 5.11 ("Hygroscopicity").

The term "solvate" as used herein and unless indicated otherwise, refers to a crystal form that incorporates a solvent in the crystal structure. When the solvent is water, the solvate is often referred to as a "hydrate". The solvent in a solvate may be present in either a stoichiometric or in a non-stoichiometric amount.

As used herein, and unless stated otherwise, the term "powder" or "powdery" refers to a solid compound in the forms of particles or granules, wherein the particles or granules can be poured. Preferably, the powders are solid, loose and dry particles.

As used herein, and unless indicated otherwise, the term "polymorphic stability" in relation to the crystalline forms of Fidaxomycin means that there is less than 20%, 10%, 5%, 1%, 0.5% or 0.1% conversion of crystalline Fidaxomycin to any other solid state form of Fidaxomycin under the specified conditions, as measured by PXRD. In some embodiments, the conversion is 0.5%-20%, 0.5%-10% or 0.5%-5% or 0.5%-1% or 0.1%-1%, or 0.1%-0.5%.

As used herein, and unless indicated otherwise, the term "Fidaxomycin" refers to the essentially chemically pure molecule of Formula I. Essentially pure in the context of the present invention means a chemical purity of at least 95%, >98%, >98.5% or even >99%, as measured by HPLC (area %, detection at 230 nm).

HPLC analytical methods are generally designed to use UV absorption at a given wavelength for recording the presence and the amount of a compound in a sample passing the detector at any given point in time. For example, the primary output of any HPLC run with standard equipment will be an area percentage of the respective peak in the UV detection chromatogram, i.e., the area under the curve (AUC). Particularly in the absence of any detailed information on the specific extinction coefficient of a given compound, the percent area values obtained by HPLC are typically equated with a "% by weight" value, i.e. without applying any correction factor. For example, the AUC percent value for a single peak (eluted at a certain retention time) will then correspond to the weight percent proportion of the compound in the sample.

As used herein, the term "reference standard" refers to a compound that may be used both for quantitative and qualitative analysis of an active pharmaceutical ingredient. For example, the retention time of the compound in HPLC allows for setting a relative retention time, thus making qualitative analysis possible. The concentration of the compound in solution before injection into an HPLC column allows for comparison of the areas under the peaks in an HPLC chromatogram, thus making quantitative analysis possible.

Although some of the knowledge of those in the art regarding reference standards has been described in general terms up to this point, those skilled in the art also understand that the detector response can be, for example, the peak heights or integrated peak areas of a chromatogram obtained, e.g., by UV or refractive index detection, from the eluent of an HPLC system or, e.g. flame ionization detection or thermal conductivity detection, from the eluent of a gas chromatograph, or other detector response, e.g., the UV absorbence, of spots on a fluorescent TLC plate. The position of the reference standard may be used to calculate the relative retention time for the compound and other impurities.

As used herein, and unless indicated otherwise, the term 'vvm' refers to the volume of the air ($Nm^3$/hrs) that reaches the fermented broth (Kg—volume) during the time (minutes) of the fermentation process. e.g., 0.5 vvm means, that the aeration during the fermentation process, wherein the fermented broth is 100 kg, is 50 Nl/min (3 $Nm^3$/hrs).

The present invention encompasses a crystalline form of Fidaxomycin, designated as Form Z. Form Z can be characterized by data selected from one or more of the following: a powder X-ray diffraction pattern having peaks at: 4.2, 7.7, 8.2, 11.2 and 15.6 degrees two theta±0.2 degrees two theta; a powder X-ray diffraction pattern substantially as depicted in FIG. 1; and by combinations of these data.

Figure 8:
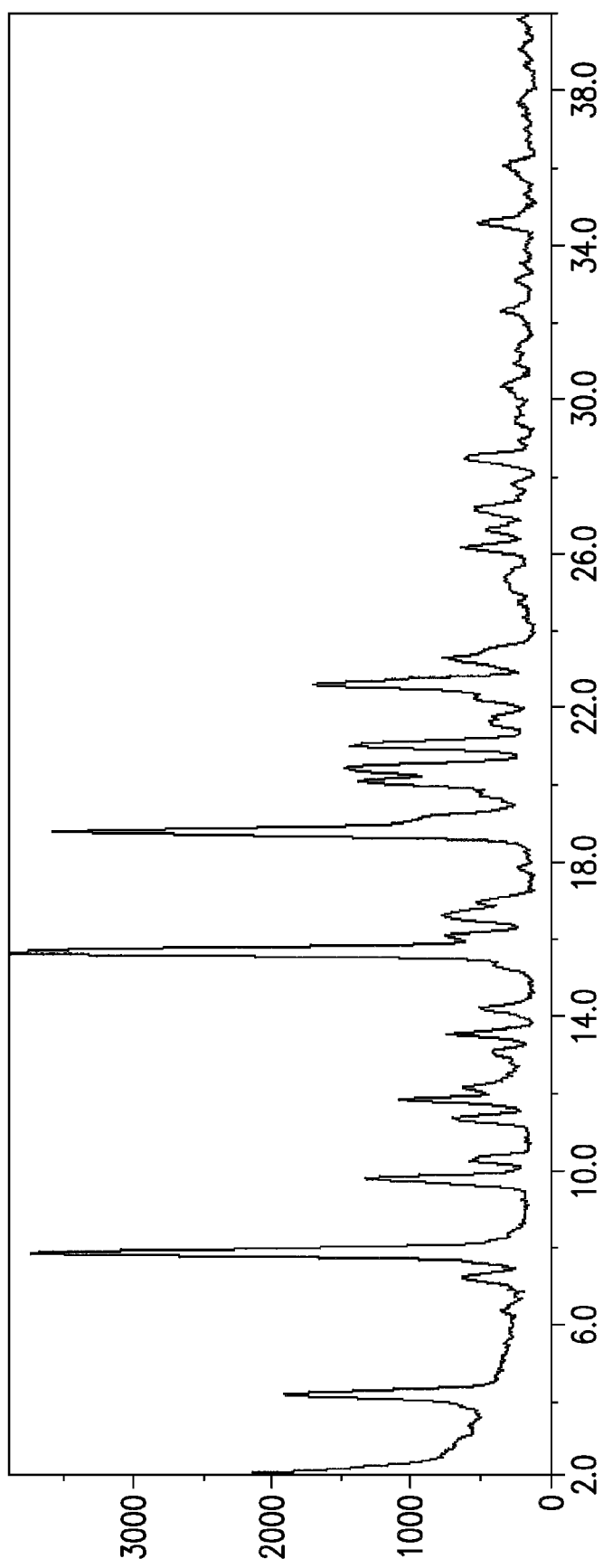
FIG. 8 shows a typical PXRD pattern for crystalline Fidaxomycin form Z (modification acetonitrile).

Alternatively, Form Z can be characterized by data selected from one or more of the following: a powder X-ray diffraction pattern having peaks at: 4.1, 9.7, 10.2, 11.2 and 15.6 degrees two theta±0.2 degrees two theta; a powder X-ray diffraction pattern substantially as depicted in FIG. 8; and by combinations of these data.

Figure 2:
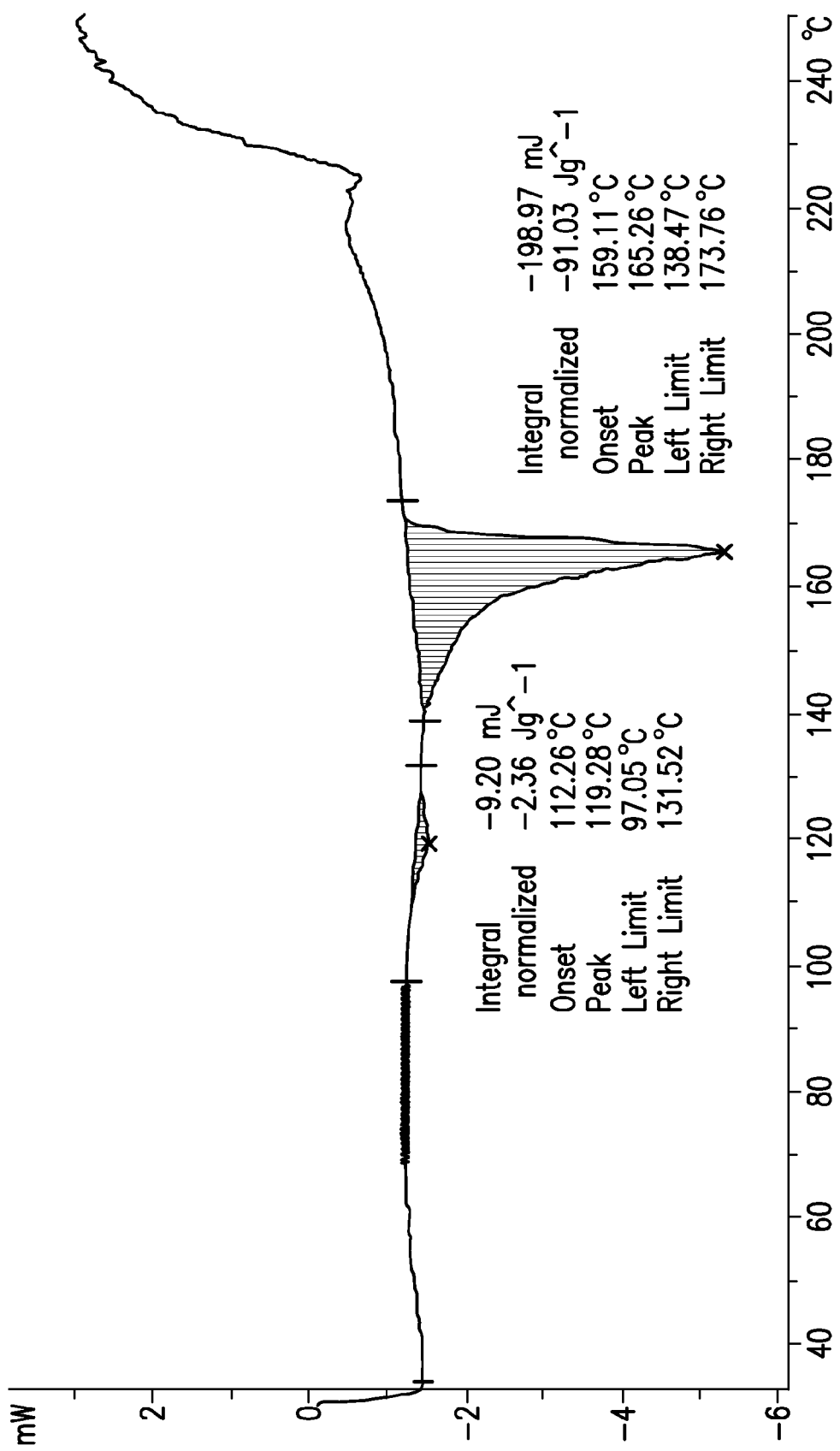
FIG. 2 shows a typical DSC curve for crystalline Fidaxomycin form Z (modification acetone).
Figure 3:
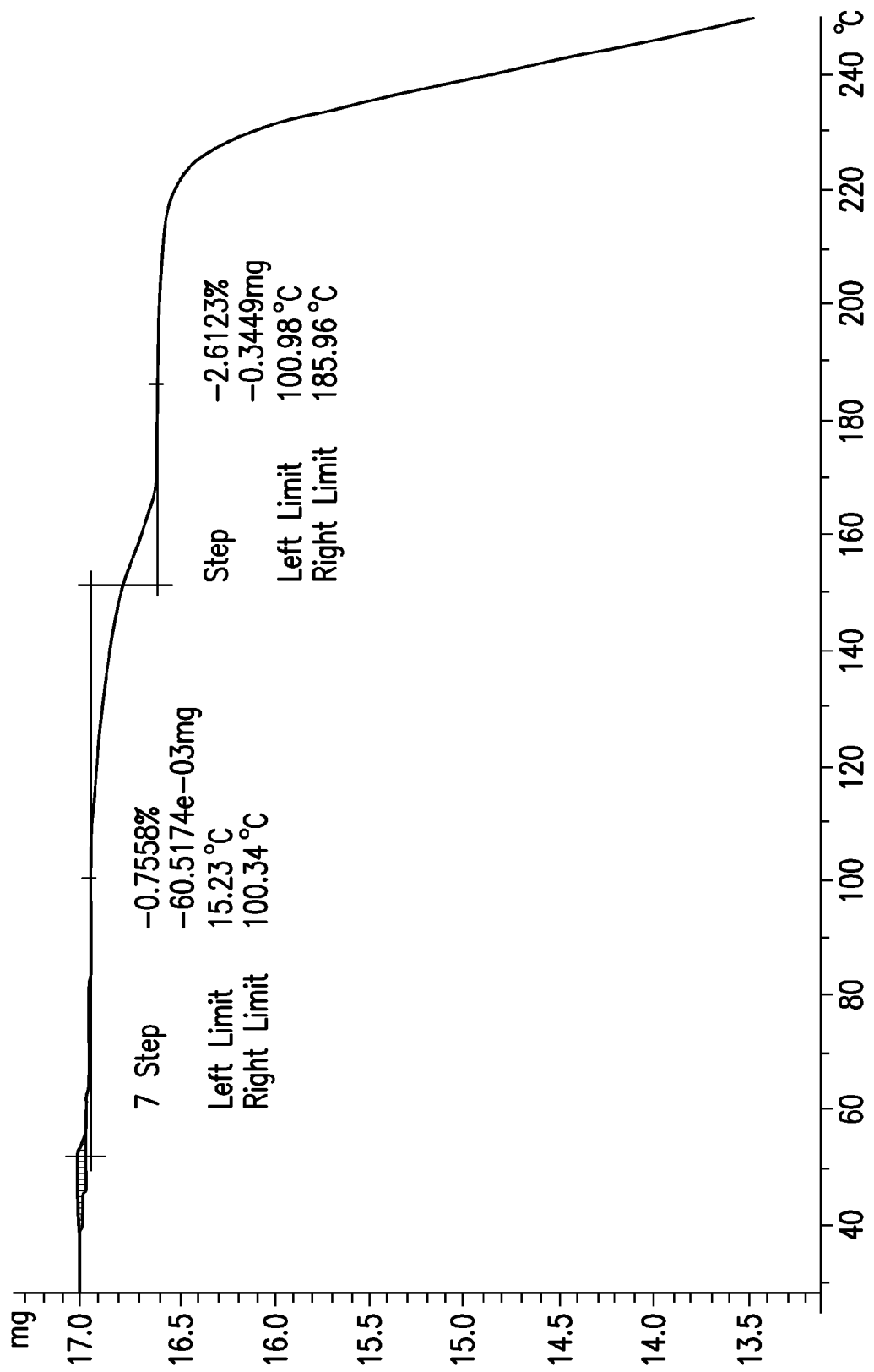
FIG. 3 shows a typical TGA curve for crystalline Fidaxomycin form Z (modification acetone).

Form Z can be further characterized by data selected from: a powder X-ray diffraction pattern having peaks at 4.2, 7.7, 8.2, 11.2 and 15.6 degrees two theta±10.2 degrees two theta and also having any one, two, three or four additional peaks selected from PXRD peaks at: 9.8, 10.3, 14.3 and 18.8 degrees two theta±0.2 degrees two theta; a DSC thermogram substantially as depicted in FIG. 2; a DSC endothermic peak at about 115-120° C. and DSC melting onset at about 160-165° C.; a TGA thermogram substantially as depicted in FIG. 3; and by combinations of these data. The above described DSC and TGA data were measured when form Z was produced from acetone.

Alternatively, Form Z can be characterized by data selected from: an X-ray powder diffraction pattern having peaks at 4.1, 9.7, 10.2, 11.2 and 15.6 degrees two theta±0.2 degrees two theta±0.2 degrees two theta and also having any one, two or three additional peaks selected from PXRD peaks at: 7.8, 14.1 and 18.7 degrees two theta±0.2 degrees two theta.

Form Z can be characterized by any combination of the above data.

Form Z can be an acetone solvate or an acetonitrile solvate.

Preferably, Fidaxomycin form Z comprises Fidaxomycin with a chemical purity of at least 95%, or even at least 98% (by HPLC).

As discussed above, Fidaxomycin Form Z has advantageous properties. In particular, the crystalline Fidaxomycin Form Z of the present invention appears to be a good intermediate in the preparation of form Z1 which itself has advantageous properties as further described herein.

The present invention also encompasses a crystalline form of Fidaxomycin, designated as Form Z1.

Figure 4:
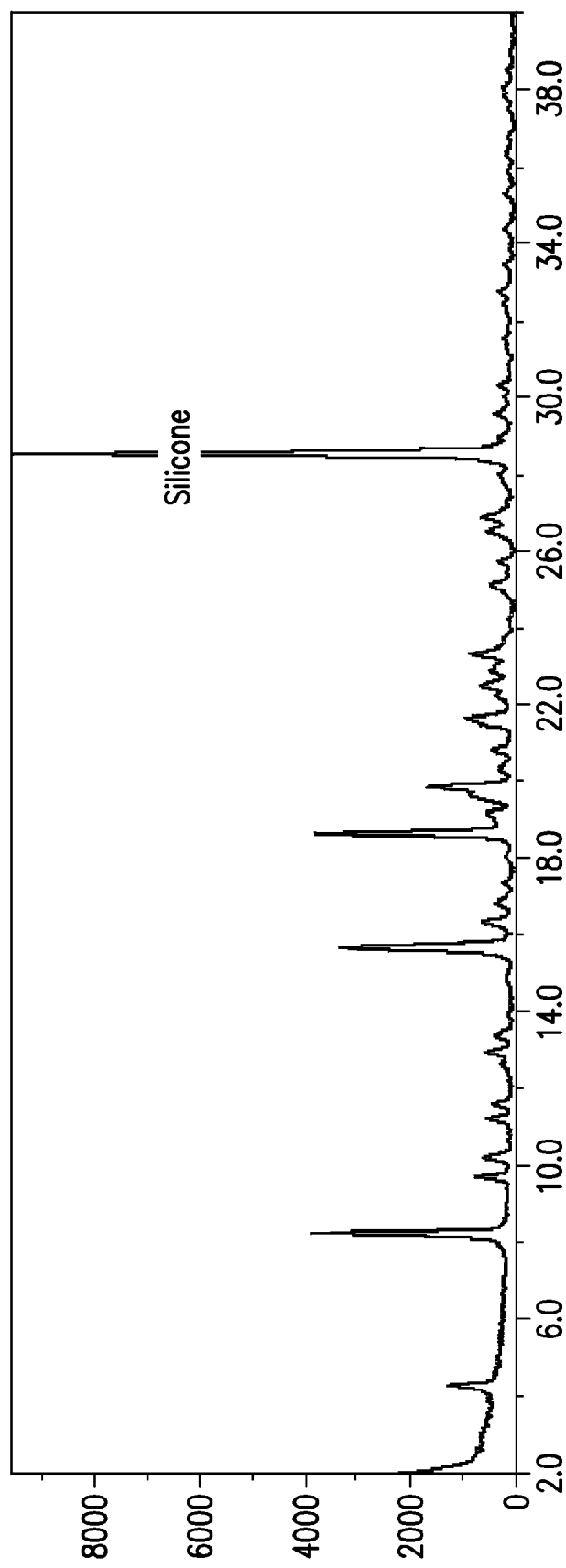
FIG. 4 shows a typical PXRD pattern for crystalline Fidaxomycin form Z1.

The present invention encompasses a crystalline form of Fidaxomycin, designated as Form Z1. Form Z1 can be characterized by data selected from: a powder X-ray diffraction pattern having peaks at: 4.3, 8.2 and 11.2±0.2 degrees two theta; by a powder X-ray diffraction pattern substantially as depicted in FIG. 4; a solid-state $^{13}$C NMR spectrum having characteristic peaks at 163.8, 129.1, 108.6, 94.4 and 60.3±0.2 ppm; a solid state $^{13}$C NMR spectrum having chemical shift differences between said characteristic peaks and a peak at 100.2±0.2 ppm of 63.6, 28.9, 8.4, −5.8 and −39.9±0.1 ppm, respectively; a solid-state $^{13}$C NMR spectrum substantially as depicted in FIG. 10; a Raman spectrum having characteristic peaks at 2993, 2974, 1749, 1721, 1649, 1594, 1572, 1451, 1257 and 587±4 $cm^{-1}$; a Raman spectrum substantially as depicted in FIG. 11; and by combinations thereof.

Form Z1 can be characterized by an X-ray powder diffraction pattern having peaks at 4.3, 8.2 and 11.2 degrees two theta±0.2 degrees two theta and also having any one, two, three, four or five additional peaks selected from PXRD peaks at: 9.7, 10.2, 15.6, 18.8 and 19.0 degrees two theta±0.2 degrees two theta.

Figure 10:
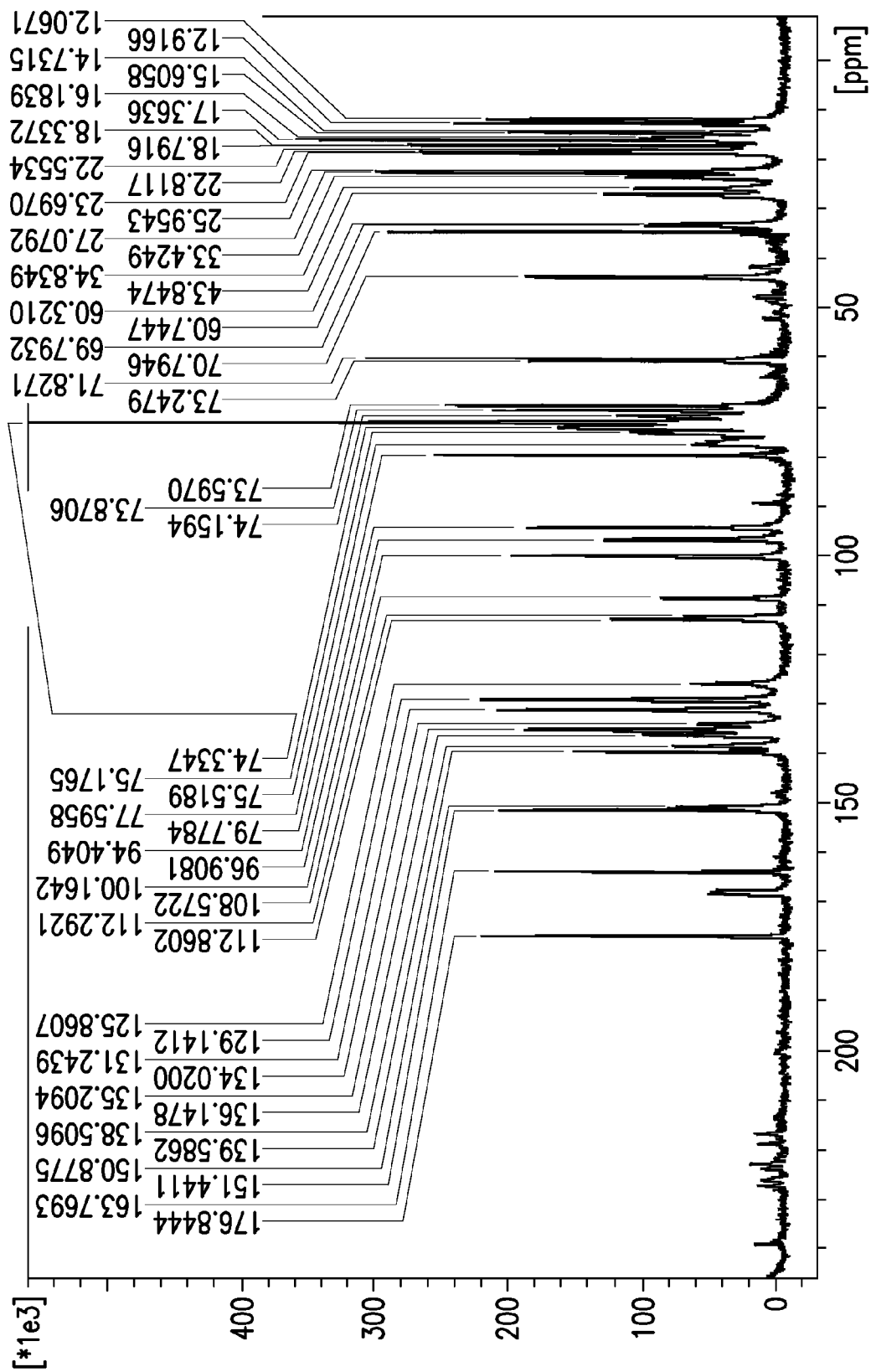
FIG. 10 shows a typical solid state $C^{13}$ NMR spectrum of Fidaxomycin form Z1.

Form Z1 can be further characterized by data selected from one or more of the following: a solid-state $^{13}$C NMR spectrum having characteristic peaks at 163.8, 129.1, 108.6, 94.4 and 60.3±0.2 ppm; a solid state $^{13}$C NMR spectrum having chemical shift differences between said characteristic peaks and a peak at 100.2±0.2 ppm of 63.6, 28.9, 8.4, −5.8 and −39.9±0.1 ppm, respectively; a solid-state $^{13}$C NMR spectrum substantially as depicted in FIG. 10; and by combinations of these data.

Figure 11:
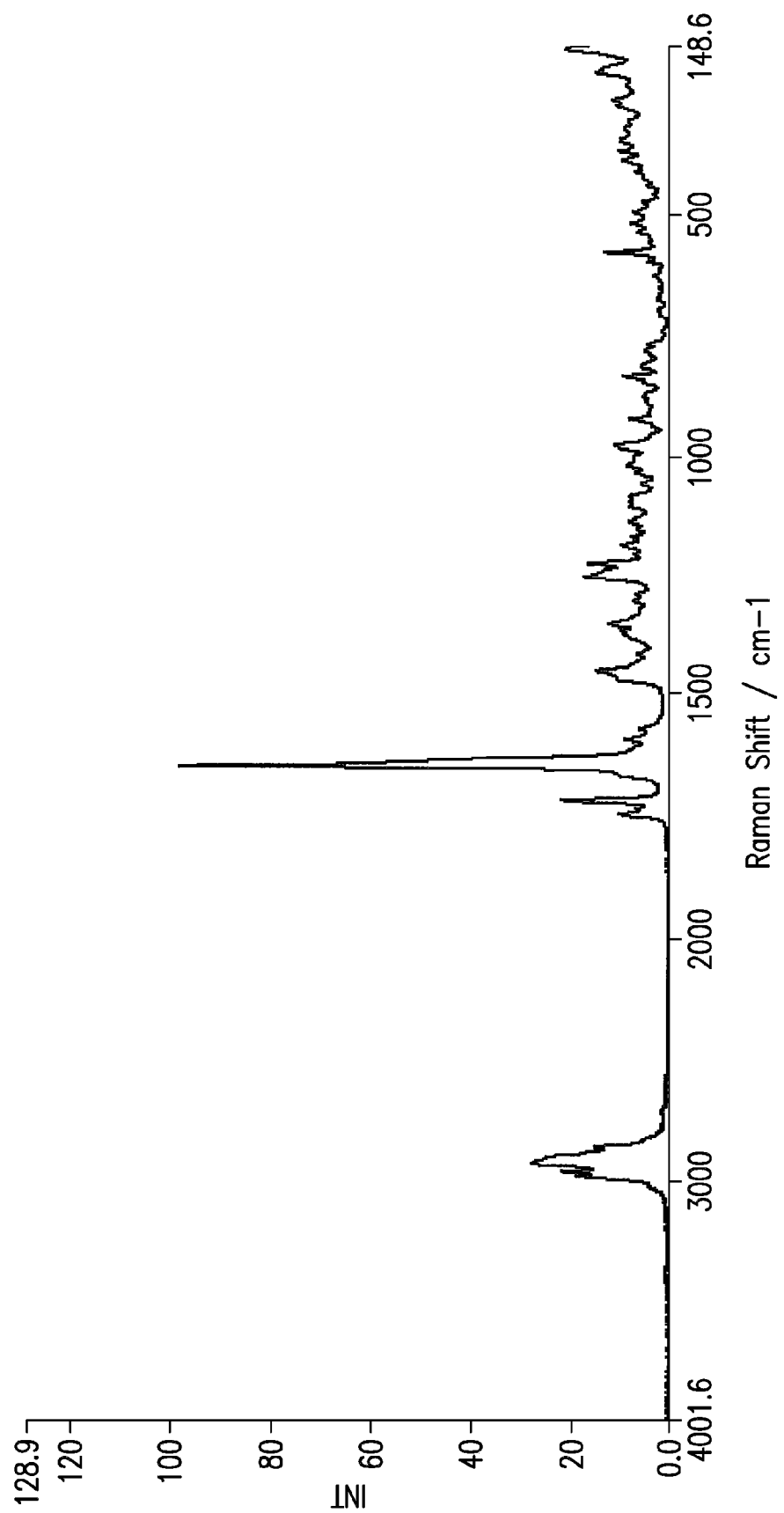
FIG. 11 shows a typical Raman spectrum of Fidaxomycin form Z1.
Figure 12:
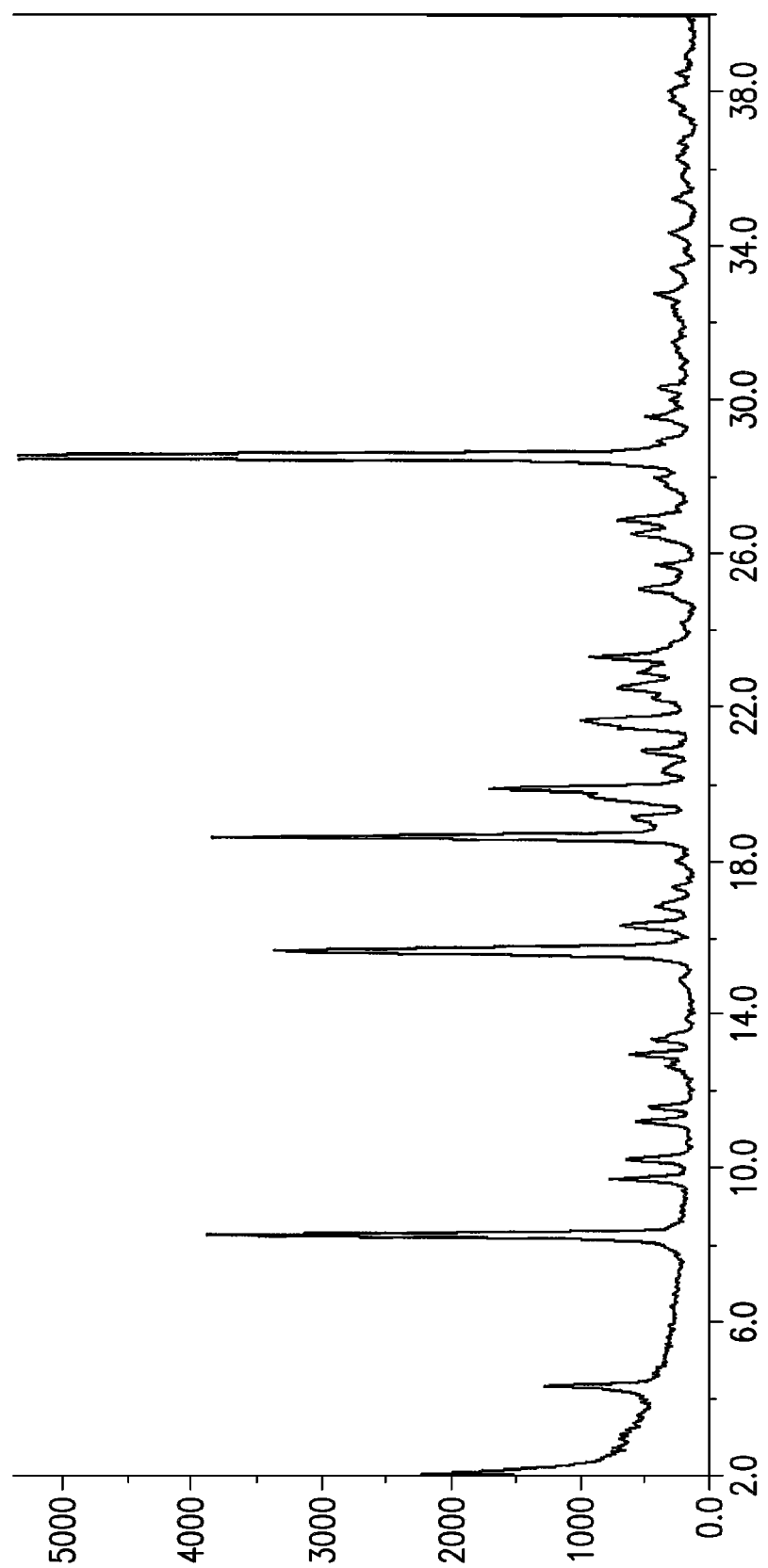
FIG. 12 shows a typical PXRD pattern for crystalline Fidaxomycin form Z1 (zoomed).
Figure 13:
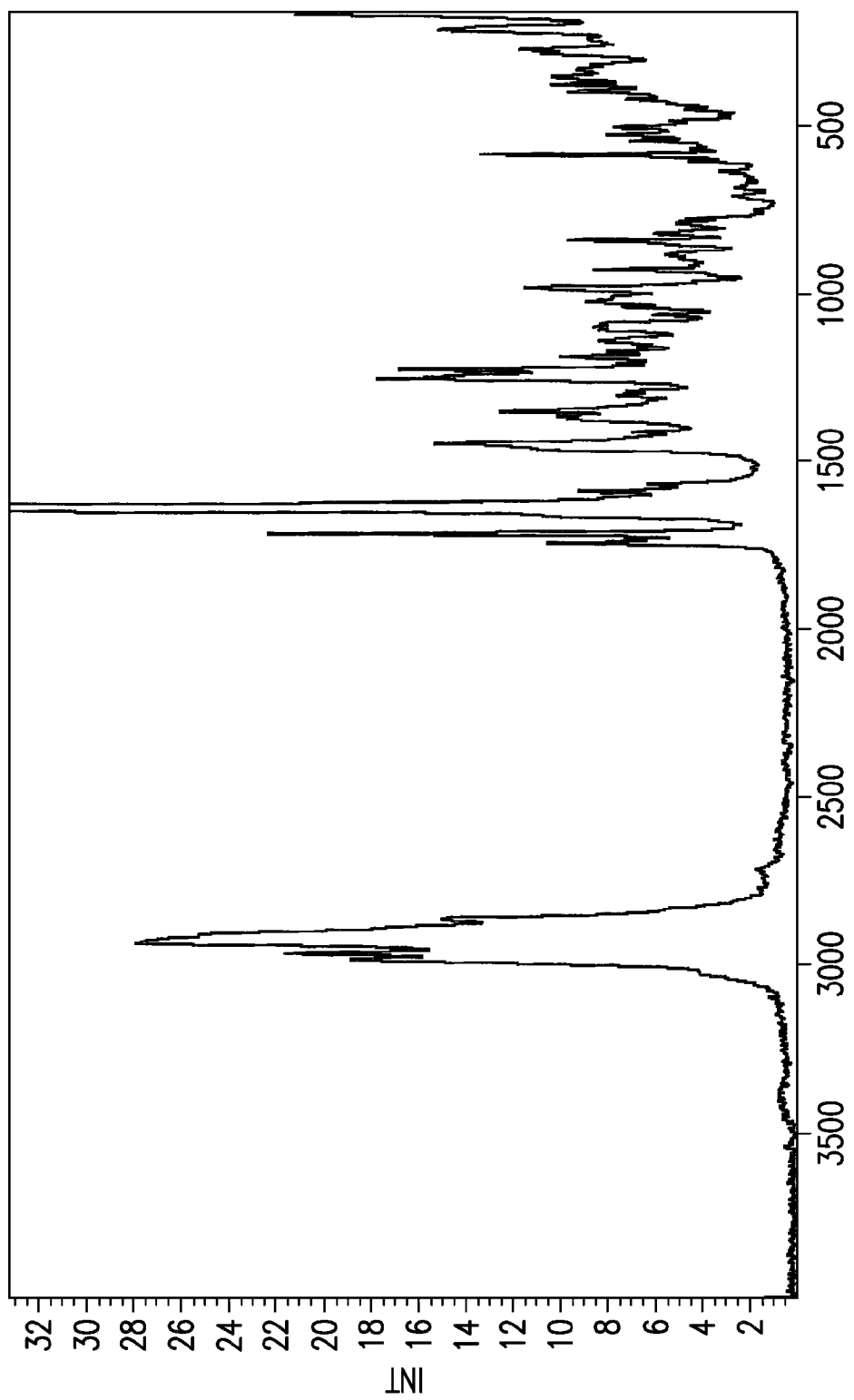
FIG. 13 shows a typical Raman spectrum of Fidaxomycin form Z1 (zoomed).

Form Z1 can be further characterized by data selected from one or more of the following: a Raman spectrum having characteristic peaks at 2993, 2974, 1749, 1721, 1649, 1594, 1572, 1451, 1257 and 587±4 $cm^{-1}$; a Raman spectrum substantially as depicted in FIG. 11; and by combinations thereof.

Figure 5:
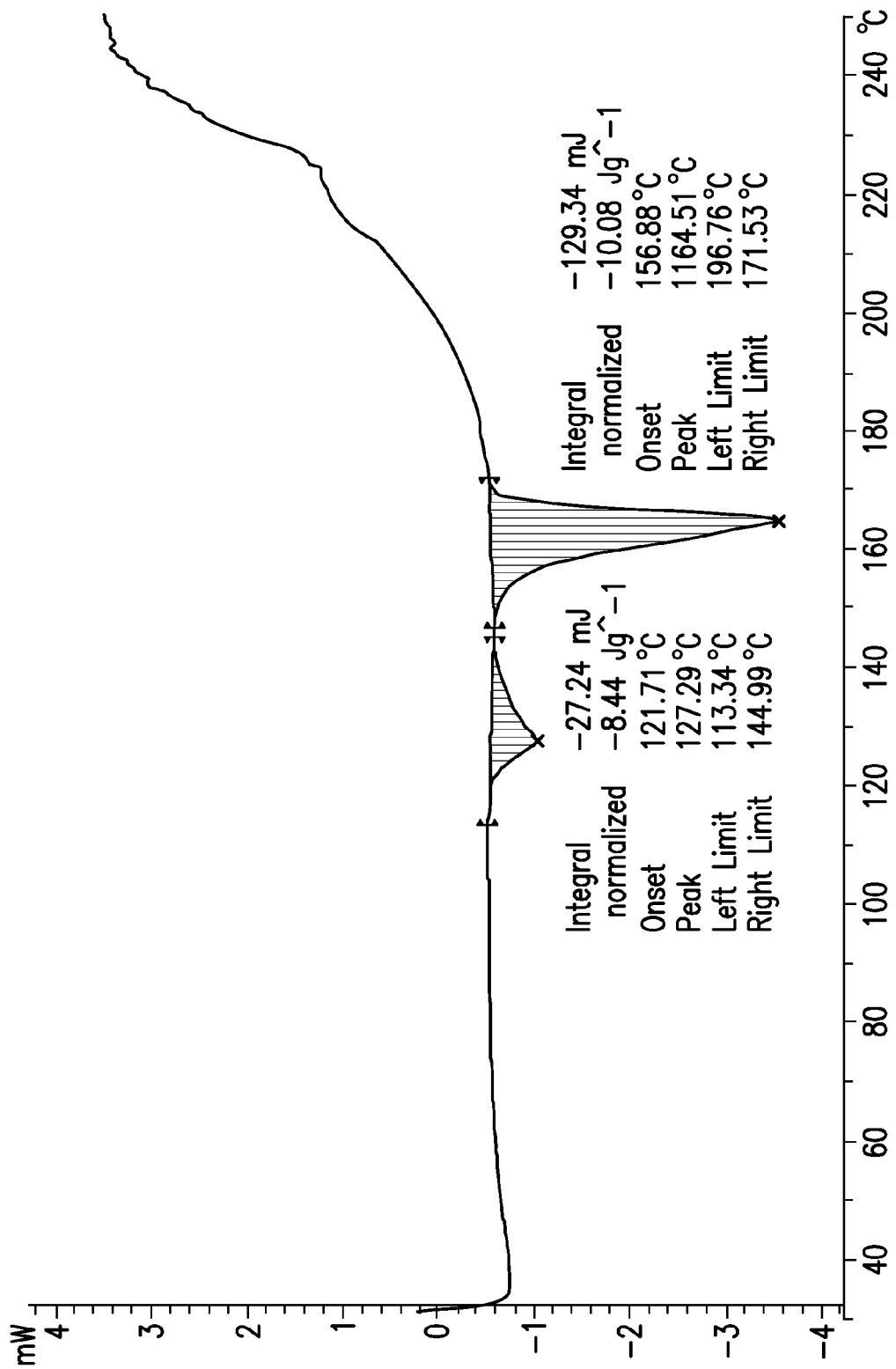
FIG. 5 shows a typical DSC curve for crystalline Fidaxomycin form Z1.
Figure 6:
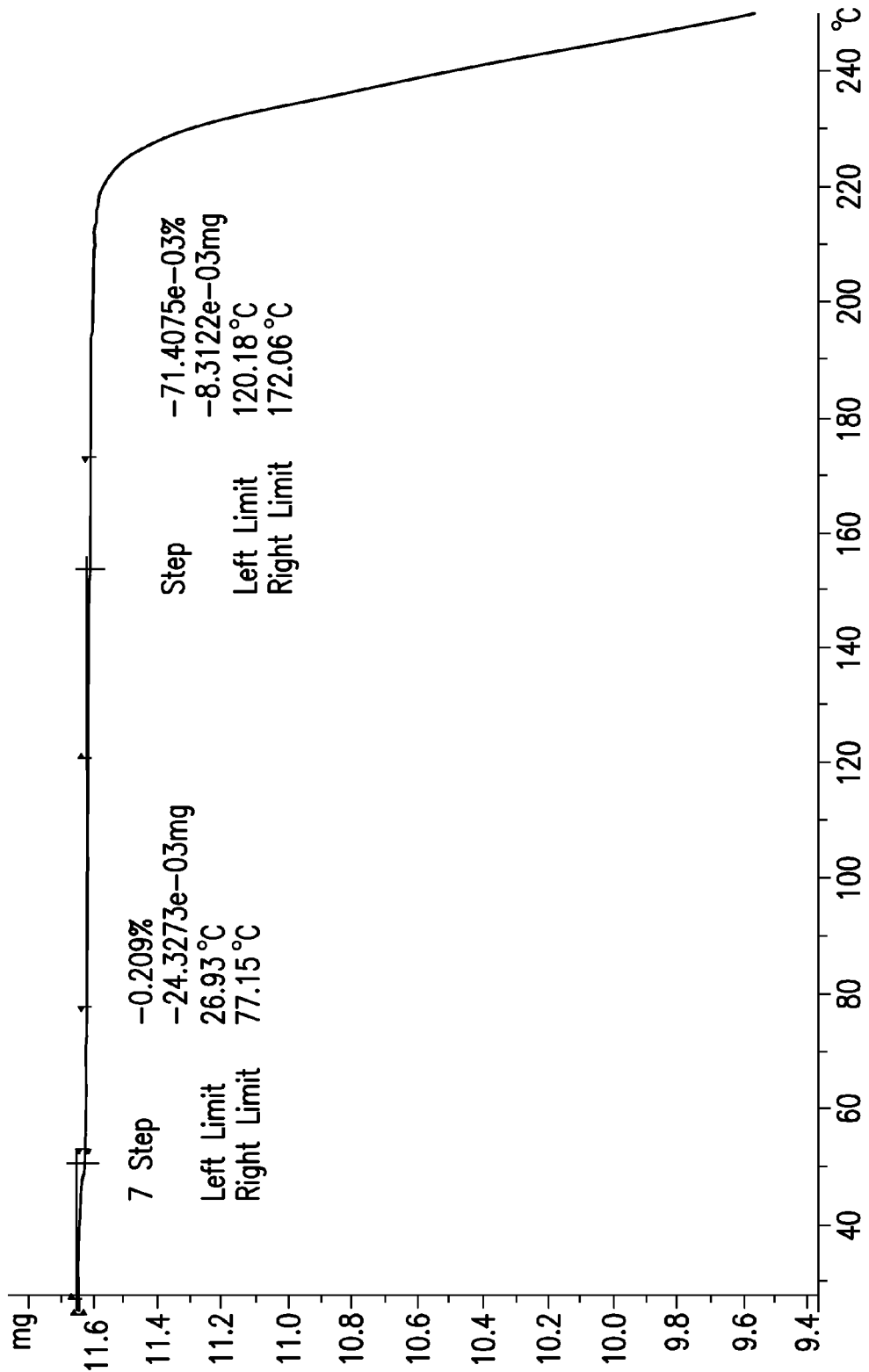
FIG. 6 shows a typical TGA curve for crystalline Fidaxomycin form Z1.

Form Z1 can be further characterized by data selected from one or more of the following: a DSC thermogram substantially as depicted in FIG. 5; a DSC endothermic peak at about 127-130° C. and DSC melting onset at about 164° C.; a TGA thermogram substantially as depicted in FIG. 6; and by combinations of these data.

Figure 9:
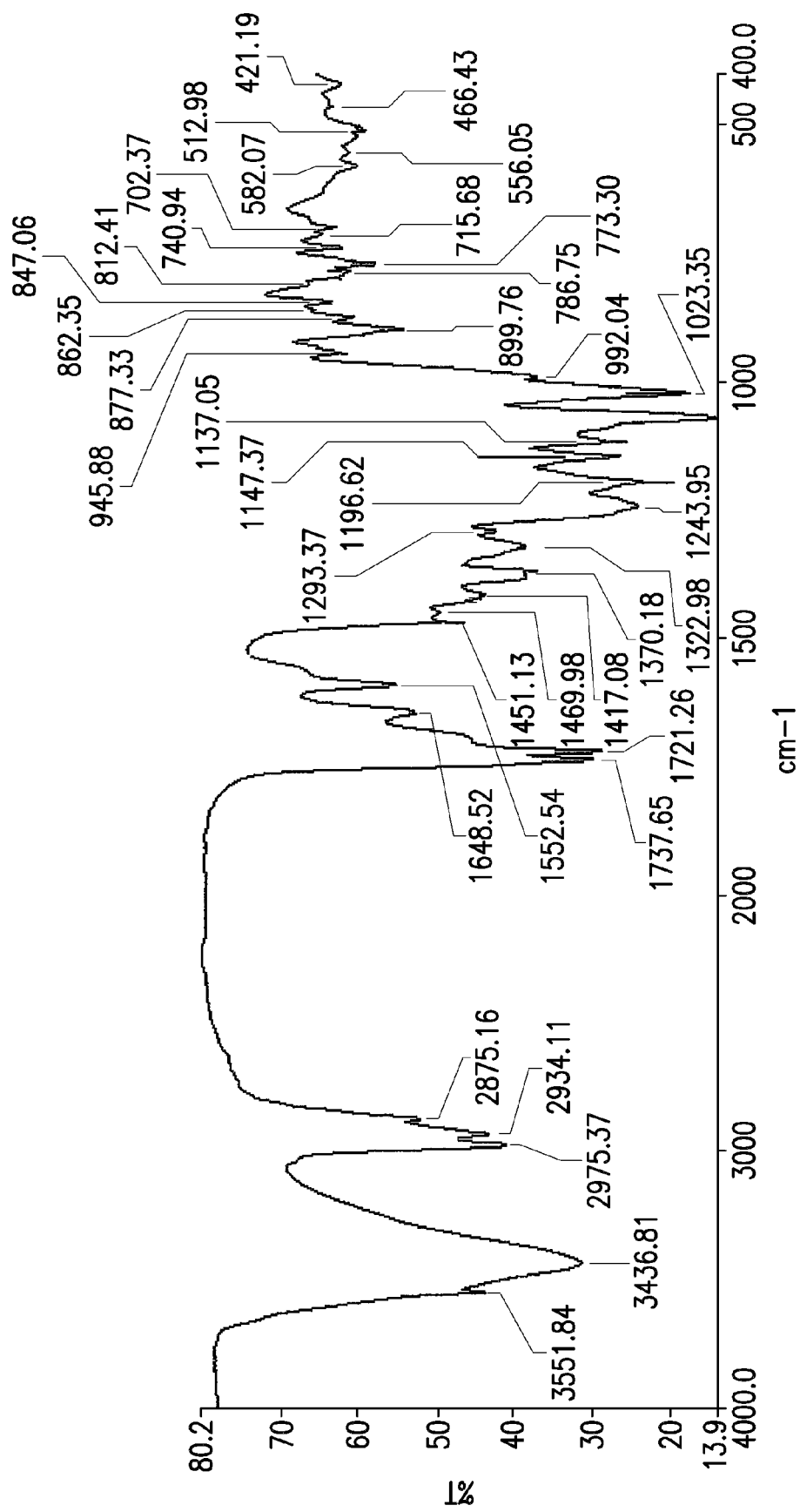
FIG. 9 shows a typical FT-IR spectrum of Fidaxomycin form Z1.

Form Z1 can be further characterized by data selected from one or more of the following: a FT-IR spectrum having characteristic peaks at 3551, 3437, 1738 and 1721±4 $cm^{-1}$; a FT-IR spectrum substantially as depicted in FIG. 9; and by combinations thereof.

Form Z1 crystals can be further characterized by a triclinic space group P1 with two symmetry independent molecules of Fidaxomycin having a unit cell with the parameters a=14.2839 Å, b=20.8214 Å, c=9.5188 Å, α=91.02°, β=90.55°, γ=100.59°, and cell volume 2782.1 Å³, as determined by synchrotron radiation at wavelength 0.43046 Å at a temperature of 275 K; or by a triclinic space group P1 with two symmetry independent molecules of fidaxomycin having a unit cell with the parameters a=14.280 Å, b=20.821 Å, c=9.530 Å, α=91.7³°, β=90.3⁹°, and γ=100.4⁶° as determined by Le-Bail fit at ambient temperature.

Preferably, Fidaxomycin form Z1 comprises Fidaxomycin with a chemical purity of >95%, >98%, or even >99% (by HPLC).

The above described form Z1 can be obtained by desolvatation of form Z.

Form Z1 can be characterized by any combination of the above data.

Form Z1 can be an anhydrous form.

As discussed above, Fidaxomycin Form Z1 has advantageous properties. In particular, the crystalline Fidaxomycin Form Z1 of the present invention is non-hygroscopic. When performing the hygroscopicity test according to the European pharmacopeia 5.11, the mass increase of Form Z1 was below about 0.2%. The advantageous of form Z1 as non-hygroscopic material provides better processing of Fidaxomycin in formulation. e.g., being less sticky and stable following granulation procedure.

In addition, form Z1 possesses excellent stability in formulations. The ability to retain the anhydrous polymorph provides an opportunity to improve the performance characteristic in formulation e.g. dissolution profile and bioavailability.

Figure 7:
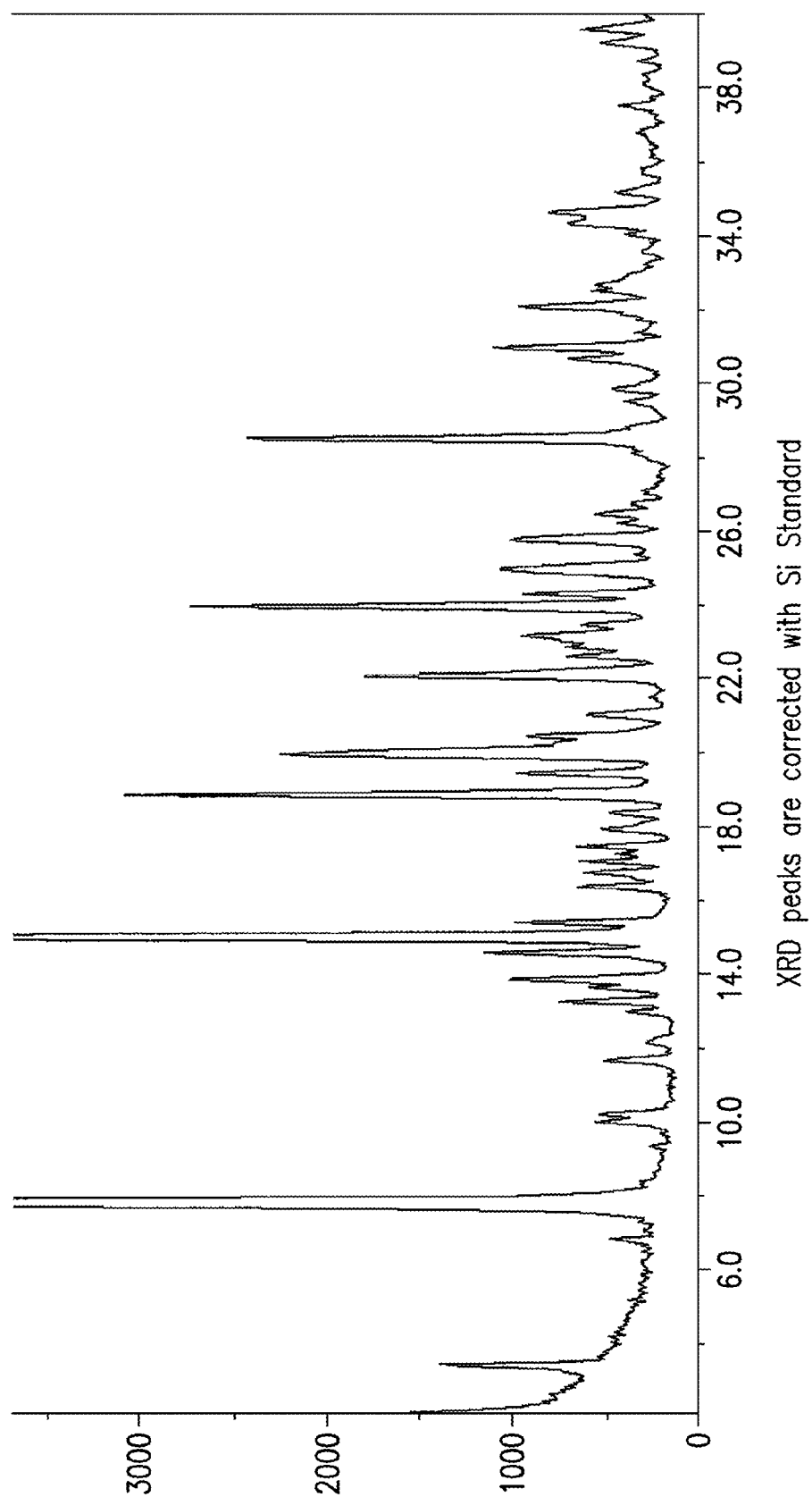
FIG. 7 shows a typical PXRD pattern for crystalline Fidaxomycin form C.

The present invention encompasses a crystalline form of Fidaxomycin, designated as Form C. Form C of Fidaxomycin can be characterized by data selected from one or more of the following: a powder X-ray diffraction pattern having peaks at: 6.8, 7.9, 10.0, 10.2, 12.2, 13.4, 14.6, 15.4, 16.4, 17.5, 18.4 and 23.1 degrees two theta±0.1 degrees two theta; a powder X-ray diffraction pattern substantially as depicted in FIG. 7; and by combinations of these data.

Preferably, Form C of Fidaxomycin is highly chemically pure and highly crystalline, i.e., Form C of Fidaxomycin comprises Fidaxomycin with a chemical purity of >98%, >99% or even >99.3% (by HPLC).

As discussed above, Form C of Fidaxomycin has advantageous properties. In particular, Form C of Fidaxomycin of the present invention can be reproduced in a high quality, i.e., chemical and polymorphical purity. The X-ray powder diffraction pattern of Form C is obtained in high crystallinity, as indicated by a high resolution PXRD pattern with relatively sharp, defined peaks. In addition, Form C is stable under extreme conditions.

The above described Form C of Fidaxomycin can be obtainable by a process comprising: a) providing a solution of Fidaxomycin having a chemical purity of >95%, or preferably >98% by HPLC in methanol, b) heating said solution to a temperature of about 55° C. to about 60° C., c) adding water to the heated solution, d) maintaining the temperature of the heated solution at about 55° C. to about 60° C. for a period of about an hour and e) cooling the heated solution to a temperature of about 15° C. to obtain a suspension comprising the crystalline Form C. The suspension may be further maintained at 15° C. for a period of about 2 hours.

The added water in step b) can be in a ratio of about 1:2 to about 1:3 to the methanol in step a), respectively.

The above process for the preparation of crystalline Form C of Fidaxomycin may further comprise recovery of said crystalline Form C from the suspension. The recovery may be done, for example, by filtering the suspension comprising said crystalline Form C, washing and drying of the crystalline product. Preferably, washing is done with a mixture of methanol:water. Preferably, drying is done under vacuum. Preferably, drying is performed at a temperature of about 50° C. Preferably, drying is done overnight.

The present invention also encompasses crystalline anhydrous Fidaxomycin.

The present invention encompasses crystalline Fidaxomycin acetone solvate.

The present invention encompasses crystalline Fidaxomycin acetonitrile solvate.

The above solid state forms of Fidaxomycin can be used to prepare pharmaceutical compositions and pharmaceutical formulations.

The present invention further encompasses 1) a pharmaceutical composition comprising one or more of the solid state forms described herein; 2) a pharmaceutical formulation comprising one or more of the solid state forms described herein, or a pharmaceutical composition comprising one or more of the solid state forms described herein, and at least one pharmaceutically acceptable excipient; 3) a process to prepare such formulations comprising combining the above-described solid state forms or pharmaceutical compositions and at least one pharmaceutically acceptable excipient; 4) the use of one or more of the solid state forms described herein in the manufacture of a pharmaceutical composition or formulation; and 5) a method for the treatment of *Clostridium difficile* infection, or CDI, also known as *Clostridium difficile*-associated disease, or CDAD. The pharmaceutical composition can be useful for preparing a medicament. The present invention also provides the use of the crystalline forms or the pharmaceutical compositions as described herein for use as a medicament.

The present invention also encompasses formulations comprising a pharmaceutical composition according to the invention. Examples of the formulation include medicaments in the form of tablets or capsules comprising the pharmaceutical composition, useful for the treatment of a person suffering from *Clostridium difficile* infection, or CDI, also known as *Clostridium difficile*-associated disease, or CDAD.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Powder X-Ray Diffraction (PXRD) Method

PXRD peaks referred to throughout and in the examples below, were obtained using an ARL X-ray powder diffractometer model X'TRA-030, equipped with Cu irradiation source=1.54056 Å, Peltier detector, round standard aluminium sample holder with round zero background quartz plate was used. Scanning parameters: Range: 2-40 degrees two-theta, continuous Scan, Rate: 3 deg./min. The accuracy of peak positions is defined as ±0.2 degrees due to experimental differences like instrumentations, sample preparations, etc. The PXRD peaks were corrected with Si standard.

Differential Scanning Calorimetry (DSC) Method

DSC 822$^e$/700, Mettler Toledo, Sample weight: 3-5 mg.

Heating rate: 10° C./min., Number of holes of the crucible: 3

In N$_2$ stream: flow rate=40 ml/min.

Scan range: 30-250° C., 10° C./minutes heating rate.

Thermogravimetric Analysis (TGA) Method

TGA/SDTA 851$^e$, Mettler Toledo, Sample weight 7-15 mg.

Heating rate: 10° C./min., in N$_2$ stream: flow rate=50 ml/min.

Scan range: 30-250° C.

GC analyses were done using AGILENT 6890N instrument equipped with Head Space7694 and FID detector.

Melting point was determined using BÜCHI-B-545 instrument with a heating rate of 1° C./min.

FT-IR Spectroscopy

Data was collected using a Perkin-Elmer Spectrum One Spectrometer, at 4 cm$^{-1}$ resolution with 16 scans, in the range of 4000-400 cm$^{-1}$. Sample was analyzed in KBr pellet. The spectrum was recorded using an empty cell as a background.

Solid-State $^{13}$C NMR Spectroscopy $^{13}$C NMR spectra were recorded at 125 MHz using a Bruker Avance II+ 500 instrument. SB probe using 4 mm rotors. Magic angle was set using KBr. Homogeneity of magnetic field was checked using adamantine. Parameters for Cross-polarization were optimized using glycine. Spectral reference set according to glycine as external standard (176.03 ppm) for low field carboxyl signal.

Scanning parameters: Magic Angle Spinning Rate: 11 kHz.

Pulse program: cp with tppm15 during decoupling.

Delay time: 5 s.

Number of scans: 1024.

Unit Cell Parameters

Powder diffraction pattern of fidaxomicin form Z1 was measured in 1.5 mm capillaries made from non-diffracting glass using synchrotron radiation at wavelength 0.43046 Å at 275 K. Indexation was independently revealed by programs DICVOL and N-TREOR.

Le-Bail fit to the laboratory powder diffraction pattern provided unit cell parameters at ambient temperature.

Raman Spectroscopy

Powder samples were filled into conical sample holder and Raman spectra were recorded on Nicolet 6700 FT-IR spectrometer with NXR FT-Raman module, equipped with 1064 nm Nd:YVO$_4$ excitation laser, CaF$_2$ beamsplitter and Ge detector.

Instrument Parameters:

Spectral range: 4000-155 cm$^{-1}$

Resolution: 4.0 cm$^{-1}$

Number of scans: 128

Sample gain: auto

Optical velocity: 0.4747

Aperture: 58.84

Laser power: 1 W

Chromatographic Conditions I:

Column: Zorbax Eclipse XDB-C8, 4.6×150 mm, 3.5 μm

Column temperature: 25° C.

Sample temperature: 15° C.

Mobile phase: A: 0.1% Acetic acid in water

B: 0.1% Acetic acid in acetonitrile

Flow rate: 1.0 ml/min

Detection wavelength: 230 nm

Injected volume: 10 μl

Detection time: 25 min

Diluent: Acetonitrile

Gradient Table

| Time (min) | Eluent A (%) | Eluent B (%) |
|---|---|---|
| 0 | 60 | 40 |
| 3 | 50 | 50 |
| 14 | 39 | 61 |
| 18 | 15 | 85 |
| 19 | 15 | 85 |
| 21 | 60 | 40 |
| 25 | 60 | 40 |

Chromatographic Conditions II:

Column: Zorbax Eclipse XDB-C8, 4.6×150 mm, 3.5 μm

Column temperature: 15° C.

Sample temperature: 15° C.

Mobile phase: A: pH=2.5H$_3$PO$_4$ solution (use cc. H$_3$PO$_4$ for the pH optimalization)

B: H$_3$PO$_4$ in acetonitrile (add the same volume of cc. H$_3$PO$_4$ as the A eluent)

Flow rate: 1.0 ml/min

Detection wavelength: 230 nm

Injected volume: 10 μl

Detection time: 23 min

Diluent: Acetonitrile

Gradient Table

| Time (min) | Eluent A (%) | Eluent B (%) |
|---|---|---|
| 0 | 60 | 40 |
| 5 | 47 | 53 |
| 15 | 45 | 55 |
| 18 | 5 | 95 |
| 20 | 5 | 95 |
| 21 | 60 | 40 |
| 23 | 60 | 40 |

Standard Stock Solution:

Weigh accurately approximately 10.0 mg of Fidaxomicin reference standard into a 20.0 ml volumetric flask, dissolve and fill it to the volume with acetonitrile.

Standard Solution:

Pipette 5.0 ml of the stock solution into a 10.0 ml volumetric flask and fill it to the volume with acetonitrile.

Sample Preparation:

Weigh accurately approximately 10.0 mg of Fidaxomicin sample into a 20.0 ml volumetric flask, dissolve and fill it up to volume with acetonitrile.

Pipette 5.0 ml of the stock solution into a 10.0 ml volumetric flask and fill it to the volume with acetonitrile.

EXAMPLES

Example 1

General Procedure for the Preparation of Crude Fidaxomycin

Fidaxomycin was prepared by:
i) culturing a microorganism in a nutrient medium to accumulate Fidaxomycin in the nutrient medium;
ii) isolating crude Fidaxomycin from the nutrient medium by methods known from the art;
iii) purifying Fidaxomycin by reversed phase chromatography using a mixture of acetonitrile, water and acetic acid as eluent; and
iv) isolating the purified Fidaxomycin from the fractions.

*Actionplanes deccanenesis* was used during the cultivation. The nutrient medium comprises the following combination based on weight: from about 0% to about 5% Sucrose; from about 0% to about 3% Starch; from about 0.1% to about 1.0% Soy peptone; from about 2% to about 5% Cotton seed meal; from about 0.01% to about 0.1% Potassium-dihydrogen Phosphate; from about 0.05% to about 0.5% Dipotassium-hydrogen Phosphate; from about 0.05% to about 0.5% Antifoam agent; from about 0% to about 2% Amberlite XAD-16N resin. The preferred temperature of the cultivation is from 28 to 32° C., and the pH is between 6.0 and 8.0. During the cultivation C-source is continuously fed.

The Fidaxomycin fermentation production can also be done by the following procedure:

The Fidaxomycin fermentation production can include a step of inoculation followed by fermentation as follows:

Inoculation: *Actinoplanes deccanenesis* strain is inoculated into the seed medium. The inoculation parameters are adjusted and maintained until the inoculum transferred to the main fermentation. The inoculum medium comprises: from about 0 to about 5% glucose, from about 0 to about 1% yeast extract, from about 0 to about 1% soy peptone, from about 0 to about 0.5% $CaCo_3$, from about 0 to about 0.2% $MgSO_4.7H_2O$, from about 0 to about 0.2% $K_2HPO_4$, from about 0 to about 0.2% KCl, from about 0 to about 0.3% Polypropylene glycol. The pH is adjusted by adding Hydrochloric acid and/or Sodium/potassium hydroxide.

Inoculation Parameters:

| Parameter | |
|---|---|
| Tip speed: | 1.5-4 m/s |
| Temperature: | 30 ± 2° C. |
| Pressure: | 0.3-0.6 ± 0.2 bar |
| Aeration rate: | 0.5 ± 0.4 vvm |

Inoculation time: 40-48±24 hours.

At the end of the inoculation, the inoculum (or a part of it) is transferred into the sterile fermentation medium at a ratio of 8-15±5%.

Fermentation: the fermentation medium comprises: from about 0 to about 110% Sucrose/Hydrolyzed Starch, from about 0 to about 1% Soy peptone, from about 0 to about 5% Cotton seed meal, from about 0 to about 0.3% $K_2HPO_4$, from about 0 to about 0.2% $KH_2PO_4$, from about 0 to about 1% KCl, from about 0 to about 0.5% Polypropylene glycol (PPG). The pH is adjusted by adding Hydrochloric acid and/or Sodium/potassium hydroxide.

The sterile fermentation medium is seeded with the inoculum.

Feeding:

C-source is fed during the fermentation. For C-source feeding sucrose or hydrolyzed-starch can be applied. Total amount of fed C-source is 0-15% related to the initial volume.

Fermentation Parameters:

| Parameter | |
|---|---|
| Temperature: | 30 ± 2° C. |
| Pressure: | 0.3-0.5 ± 0.2 bar |
| Aeration rate: | 0.5-1.0 ± 0.3 vvm |
| Mixing (tip speed): | 3-11 m/s |

In case of foaming, sterile antifoaming agent should be added.

Fermentation time: 168-192±24 hours.

The inoculation/fermentation medium may also include from about 0% to about 2% Amberlite XAD-16N resin.

Upon completion of fermentation, the Fidaxomycin is extracted from the fermented broth with an organic solvent such as, for example, ethyl acetate, isobutyl acetate or isobutanol. The organic phase is concentrated and the Fidaxomycin is precipitated by addition of an antisolvent such as, for example, n-hexane. Optionally the precipitate can be suspended in a second antisolvent. After filtration and drying, crude Fidaxomycin is obtained.

Example 2

Procedure for the Preparation of Fidaxomycin Form Z

Fidaxomycin (253.5 mg assay: 89.1%, purity: 94.9%, amorphous) obtained by the same procedure described in Example 10 and 1 ml acetone/water (3/1) mixture were charged into a test tube. The test tube was closed and was placed in a water bath at 50° C. After the Fidaxomycin was dissolved, the solution was allowed to stand at room temperature for 4 days to produce a crystalline precipitate. The crystals were separated from the solution by filtration and washed with acetone/water (3/1). The product was dried at 50° C. in a vacuum oven overnight and then analyzed by HPLC. Assay and HPLC purity were >99% and 98.7%, respectively. Based on PXRD analysis, the product is form Z.

Example 3

Procedure for the Preparation of Fidaxomycin Form Z

Fidaxomycin (496.2 mg, assay: 85.7%, purity: 96.4%, amorphous) obtained by the same purification procedure described in Example 2 or 10 and 2 ml acetone/water (3/1) mixture were charged into a test tube. The test tube was closed and was placed in a water bath at 55° C. After the Fidaxomycin was dissolved the solution was cooled quickly by plunging the test tube into ice water. The solution was then allowed to stand at room temperature for 7 days. Crystals formed and were separated by filtration and dried at 50° C. in a vacuum oven overnight. The product was analyzed by HPLC. Assay and HPLC purity were 89.4% and 96.4%, respectively. Based on PXRD analysis, the obtained form is form Z.

Example 4

Procedure for the Preparation of Fidaxomycin Form Z

Fidaxomycin (0.4 g, assay: 94.0%, purity: 95.3%) obtained by the same purification procedure described in Example 2 or recovered from other crystallization experiments, 4.8 ml acetone and 0.5 ml deionized water were charged into a test tube. The test tube was closed and was placed in a water bath at 55° C. After the Fidaxomycin was dissolved, additional 2.7 ml deionized water was added and the solution was stirred in the bath at 55° C. After stirring for 60 minutes, the first crystals appeared. The suspension was stirred for an additional 165 minutes and the crystals were filtered off and dried at 50° C. in a vacuum oven overnight. The dried crystals were analyzed by HPLC. Assay and HPLC purity were 97.6% and 98.3%, respectively. Based on PXRD analysis, the obtained form is form Z.

Example 5

Procedure for the Preparation of Fidaxomycin Form Z

Fidaxomycin (7.5 g, assay: 95.5%, purity: 98.4%) obtained by the same purification procedure described in Example 11, 72 ml acetone and 8 ml deionized water were charged into a round bottom flask, which was heated in a water bath at 55° C. After the Fidaxomycin was dissolved, an additional 40 ml deionized water was added drop-wise to the solution with stirring in the 55° C. bath. After 130 minutes, crystals had not formed. Some wet Fidaxomycin crystals (prepared from acetone/water (60/40) mixture as described in the procedure of example 2 or 3) were added to the solution and the resulting mixture was stirred for an additional 3 hours. Crystals formed and were filtered off, washed with 20 ml acetone/water (60/40) mixture, and dried at 50° C. in a vacuum oven for about 6 hours. The dried crystals (3.07 g) were analyzed by HPLC. Assay and HPLC purity were 94.9% and 99.4%, respectively. Based on PXRD the obtained form is form Z (acetone solvate) in a mixture with form Z1 (FIG. 1).

Example 6

Procedure for the Preparation of Fidaxomycin Form Z1

Fidaxomycin (5.0 g, assay: 97.7% and purity: 98.3%), obtained by following the same purification procedure described in Example 5 or 11, was added, along with 45 ml acetone and 5 ml DI water to a round bottom flask. The flask was heated in a water bath at 55° C. After the Fidaxomycin was dissolved, an additional 40 ml DI water was added dropwise while stirring in the bath at 55° C. The first crystals appeared after addition of 36.5 ml water. The resulting suspension was stirred for an additional 2 hours (in water bath at 50° C.) followed by filtration. The collected crystals were washed with 15 ml acetone/water (50/50) mixture. The crystals were then dried under vacuum at 50° C. for 40 hours, at 60° C. for 48 hours, at 80° C. for 48 hours and finally at 100° C. for 24 hours. The dried crystals were analyzed by HPLC. Assay and HPLC purity were >99% and 99.4%, respectively. Based on PXRD analysis, the product is form Z1.

Example 7

Procedure for the Preparation of Fidaxomycin Form Z1

Fidaxomycin (10.0 g, assay: 97.7%, purity: 98.3%), obtained by the same purification procedure described in Example 6 or 11, was added, along with 90 ml acetone and 10 ml DI water to a round bottom flask. The flask was heated in a water bath at 55° C. After the Fidaxomycin was dissolved, an additional 80 ml DI water was added dropwise while stirring in the bath at 55° C. The first crystals appeared after addition of 72 ml water. The resulting suspension was stirred for an additional 2 hours (temp?) followed by filtration. The collected crystals were washed with 30 ml acetone/water (50/50) mixture. The crystals were then dried under vacuum at 60° C. for 4 hours to provide 8.59 g of Fidaxomycin. A portion (7.96 g) of this material was dried further at 100° C. for 16 hours. The dried crystals (7.92 g) were analyzed by HPLC. Assay and HPLC purity were >99% and 99.6%, respectively. Based on PXRD analysis, the product is form Z1.

Example 8

Procedure for the Preparation of Fidaxomycin Form Z1

Crude Fidaxomycin was purified by reversed phase chromatography in portions using a column packed with 400 g Diasogel SP-100-15-ODS-P and eluted with acetonitrile/H2O/AcOH (45/55/0.055) or acetonitrile/H2O/AcOH (50/50/0.05). The collected fractions were combined and were concentrated to one-half of the original volume to produce a precipitate. The precipitate was filtered, washed with water and dried under high vacuum. HPLC analysis of the off-white powder showed that the assay was 96.7% and purity was 98.9%. A 1.0 g portion of this Fidaxomycin and 10 ml acetonitrile/water (9/1) mixture were added to a test tube. After stirring for several minutes, the Fidaxomycin was dissolved resulting in an opalescent solution. An additional 0.5 g of Fidaxomycin was added and the resulting suspension was maintained at ambient temperature overnight. Crystals formed and were filtered and washed with 5 ml acetonitrile/water (9/1) mixture. The crystals were then dried at 50° C. under vacuum overnight. The dried crystals (1.0 g) were analyzed by HPLC. Assay and HPLC purity were >99% and 99.2%, respectively. Based on PXRD analysis, the obtained form is form Z1.

Example 9

Procedure for Crystalline Fidaxomycin Form C

Fidaxomicin (22.0 g, assay: 95.8, HPLC purity: 98.1%), obtained by the same purification method described in Example 6 or 11, was dissolved in 130 ml methanol. The solution was heated to 55° C. and 60 ml of DI water was added over 20 minutes. The mixture was kept at 55° C. for an hour followed by cooling to 15° C. over 150 mins. The formed suspension was kept at 15° C. for an additional 2 hours. Crystals formed and were filtered and washed with the mixture of 26 ml methanol and 12 ml of DI water. The crystals were then dried at 50° C. under vacuum overnight. The resulting material (19.3 g) was analyzed by HPLC. Assay and HPLC purity were 99.5% and 99.1%, respectively.

Example 10

Procedure for the Purification of Fidaxomycin

Crude Fidaxomycin was purified by reversed phase chromatography in portions using a column packed with Merck LiChroprep RP-18 (15-25 u) and eluted with acetonitrile/ $H_2O$/AcOH (45/55/0.055). The collected fractions containing >90% Fidaxomycin were combined, and the acetonitrile was evaporated at room temperature, and the residual suspension was extracted three times with half volume of ethyl acetate. The upper layers were combined, and the ethyl acetate was evaporated. The residue, an off-white powder, was dried under high vacuum. HPLC analysis of the combined powders showed that the assay is 89.1% and the purity is 94.9%. PXRD analysis indicated the powder is amorphous.

Example 11

Procedure for the Purification of Fidaxomycin

Crude Fidaxomycin was purified by reversed phase chromatography using a 8 L column packed with Diasogel SP-100-15-ODS-P and eluted with acetonitrile/$H_2O$/AcOH (50/50/0.05). The collected fractions containing >93% Fidaxomycin were combined and were concentrated to about one-half of the original volume to produce a precipitate. The precipitate was filtered, washed with water and dried under high vacuum. HPLC analysis of the off-white powder showed that the assay is 95.5% and purity is 98.4%.

Example 12

Procedure for the Preparation of Fidaxomycin Form Z and Z1

Fidaxomycin (10.0 g, assay: 95.6%, purity: 95.2%), obtained by the same purification procedure described in Example 11, was suspended in acetonitrile/water (10/4, v/v) mixture at room temperature and was left on the table for overnight. Next morning it was diluted with 25 ml acetonitrile/water (10/4, v/v) mixture, the crystals were filtered off and were washed with 25 ml acetonitrile/water (10/4, v/v) mixture. The wet product was sampled and was analyzed by PXRD; on the basis of this analysis the wet product was Form Z (FIG. 8). The crystals were then dried under vacuum at 60° C. for 6 hours. The dried crystals (7.35 g) were analyzed by HPLC. Assay and HPLC purity were >99% and 98.3%, respectively. Based on PXRD analysis, the dried product is form Z1.

Example 13

Procedure for the Preparation of Fidaxomycin Form Z1

Fidaxomycin batches (770 g, assay: 97.1%, purity: 99.7% and 362.3 g, assay: 95.1%, purity: 99.7%) purified by reverse phase chromatography (obtained by the same purification procedure described in Example 11: the batches were combined in portions of about 20 g after reverse phase chromatography as described in Example 11 using a 4 L column and combining fractions containing >98% Fidaxomycin), was dissolved in 9 L acetone/water (9/1,v/v) mixture. The solution was filtered and the filter was washed with 1 L acetone/water (9/1) mixture. The solution was heated up to 50° C. and 8.95 L deionized water was added. The first crystals appeared after addition of 7.3 L water. The resulting suspension was stirred for an additional 2 hours followed by filtration. The collected crystals were washed with 3 L acetone/water (50/50) mixture. The crystals were then dried under vacuum at 60° C. for 2 hours and at 100° C. for 40 hours. Assay and HPLC purity were 99.1% and 99.5%, respectively. Based on PXRD analysis, the product is form Z1.

Example 14

Procedure for Crystalline Fidaxomycin Form C

Fidaxomycin batches (742.3 g, assay: 95.9%, purity: 99.7% and 388 g, assay: 95.1%, purity: 99.7%) purified by reverse phase chromatography (obtained by the same purification procedure described in Example 11: the batches were combined in portions of about 20 g after reverse phase chromatography as described in Example 11 using a 4 L column and combining fractions containing >98% Fidaxomycin), was dissolved in 5.5 L methanol at 40° C. The solution was filtered and the filter was washed with 1.1 L methanol. The solution was heated to 55° C. and 2750 ml of DI water was added over 25 minutes. The mixture was kept at 55° C. for an hour followed by cooling to 15° C. over 145 mins. The formed suspension was kept at 15° C. for an additional 2 hours. Crystals formed and were filtered and washed with the mixture of 880 ml methanol and 420 ml of DI water. The crystals were then dried at 60° C. under vacuum for 16.5 hours. The resulting material (1066 g) was analyzed by HPLC. Assay and HPLC purity were 98.0% and 99.7%, respectively.

Example 15

Procedure for the Preparation of Fidaxomycin Form Z1

Fidaxomycin (80.74 g, assay: >99%, purity: 99.6%) purified by reverse phase chromatography (obtained by the same purification procedure described in Example 11: the batches were combined in portions of about 20 g after reverse phase chromatography as described in Example 11 using a 4 L column and combining fractions containing >98% Fidaxomycin) was dissolved in 800 ml acetonitrile and 200 water at 60° C. The solution was filtered and 600 ml DI water was added over 20 mins. The first crystals appeared after addition of 450 ml water. The slurry was stirred for 2 hours followed by filtering off the crystals and were dried at 60° C. under vacuum for 16 hours. The resulting material was analyzed by HPLC. Assay and HPLC purity were 99.4% and 99.8%, respectively. Based on PXRD analysis, the product is form Z1.

Example 16

Procedure for the Preparation of Fidaxomycin Form Z1

Fidaxomycin batches (402 g, assay: 97.7%, purity: 99.6% and 884.6 g, assay: 99.2%, purity: 99.1%) purified by reverse phase chromatography (obtained by the same purification procedure described in Example 11: the batches were combined in portions of about 20 g after reverse phase chromatography as described in Example 11 using a 4 L column and combining fractions containing >98% Fidaxomycin), was dissolved in 16 L acetonitrile/water (4/1, v/v) mixture at 60° C. The solution was filtered and the filter was washed with 1 L acetonitrile/water (4/1, v/v) mixture and 10 L DI water preheated to 35° C. was added. The mixture was kept at 35° C. for 4 hours followed by filtering off the crystals. The crystals were washed with the mixture of 1 L acetonitrile and 1 L of DI water. The crystals were then dried at 60° C. under vacuum for 18 hours. The resulting material was analyzed by HPLC. Assay and HPLC purity were 98.7% and 99.5%, respectively. Based on PXRD analysis, the product is form Z1.

What is claimed is:

1. A crystalline form of Fidaxomycin, wherein the crystalline form is crystalline form of Fidaxomycin, designated as Form Z1, characterized by data selected from one or more of the following: a powder X-ray diffraction pattern having peaks at: 4.3, 8.2 and 11.2 degrees two theta±0.2 degrees two theta; a powder X-ray diffraction pattern substantially as depicted in FIG. 4; and by combinations of these data;

crystalline Form Z of Fidaxomycin characterized by data selected from one or more of the following: a powder X-ray diffraction pattern having peaks at: 4.1, 9.7, 10.2, 11.2 and 15.6 degrees two theta±0.2 degrees two theta; a powder X-ray diffraction pattern substantially as depicted in FIG. 8; and by combinations of these data; or crystalline form of Fidaxomycin, designated as Form C, characterized by data selected from one or more of the following: a powder X-ray diffraction pattern having peaks at: 6.8, 7.9, 10.0, 10.2, 12.2, 13.4, 14.6, 15.4, 16.4, 17.5, 18.4 and 23.1 degrees two theta±0.1 degrees two theta; a powder X-ray diffraction pattern substantially as depicted in FIG. 7; and by combinations of these data.

2. The crystalline form of Fidaxomycin of claim 1, wherein the crystalline form is Form Z1 characterized by data selected from one or more of the following: a powder X-ray diffraction pattern having peaks at: 4.3, 8.2 and 11.2 degrees two theta±0.2 degrees two theta; a powder X-ray diffraction pattern substantially as depicted in FIG. 4; and by combinations of these data.

3. The crystalline Form Z1 of claim 2, wherein said crystalline Form Z1 characterized by an X-ray powder diffraction pattern having peaks at 4.3, 8.2 and 11.2 degrees two theta±0.2 degrees two theta and also having any one, two, three, four or five additional peaks selected from PXRD peaks at: 9.7, 10.2, 15.6, 18.8 and 19.0 degrees two theta±0.2 degrees two theta.

4. The crystalline Form Z1 of claim 2, further characterized by data selected from one or more of the following: a solid-state $^{13}$C NMR spectrum having characteristic peaks at 163.8, 129.1, 108.6, 94.4 and 60.3±0.2 ppm; a solid state $^{13}$C NMR spectrum having chemical shift differences between said characteristic peaks and a peak at 100.2±0.2 ppm of 63.6, 28.9, 8.4, −5.8 and −39.9±0.1 ppm, respectively; a solid-state $^{13}$C NMR spectrum substantially as depicted in FIG. 10; and by combinations of these data.

5. The crystalline Form Z1 of claim 2, further characterized by data selected from one or more of the following: a Raman spectrum having characteristic peaks at 2993, 2974, 1749, 1721, 1649, 1594, 1572, 1451, 1257 and 587±4 cm$^{-1}$; a Raman spectrum substantially as depicted in FIG. 11; and by combinations thereof.

6. The crystalline Form Z1 of claim 2, further characterized by data selected from one or more of the following: a DSC thermogram substantially as depicted in FIG. 5; a DSC endothermic peak at about 127-130° C. and DSC melting onset at about 164° C.; a TGA thermogram substantially as depicted in FIG. 6; and by combinations of these data.

7. The crystalline Form Z1 of claim 2, further characterized by data selected from one or more of the following: a FT-IR spectrum having characteristic peaks at 3551, 3437, 1738 and 1721±4 cm$^{-1}$; a FT-IR spectrum substantially as depicted in FIG. 9; and by combinations thereof.

8. The crystalline Form Z1 of claim 2, further characterized by a triclinic space group P1 with two symmetry independent molecules of fidaxomycin having a unit cell with the parameters a=14.2839 Å, b=20.8214 Å, c=9.5188 Å, α=91.02°, β=90.55°, γ=100.59°, and cell volume 2782.1 Å$^3$, as determined by synchrotron radiation at wavelength 0.43046 Å at a temperature of 275 K; or by a triclinic space group P1 with two symmetry independent molecules of fidaxomycin having a unit cell with the parameters a=14.280 Å, b=20.821 Å, c=9.530 Å, α=91.7³°, β=90.3⁹°, and γ=100.4⁶° as determined by Le-Bail fit at room temperature.

9. The crystalline Form Z1 of claim 2, wherein said crystalline Form Z1 contains Fidaxomycin with a chemical purity by HPLC of >95%, >98%, or >99%.

10. The crystalline Form Z1 of claim 2, wherein said crystalline Form Z1 is an anhydrous form.

11. The crystalline form of Fidaxomycin of claim 1, wherein the crystalline form is Form Z characterized by data selected from one or more of the following: a powder X-ray diffraction pattern having peaks at: 4.1, 9.7, 10.2, 11.2 and 15.6 degrees two theta±0.2 degrees two theta; a powder X-ray diffraction pattern substantially as depicted in FIG. 8; and by combinations of these data.

12. The crystalline Form Z of claim 11, wherein said crystalline Form Z characterized by data selected from: an X-ray powder diffraction pattern having peaks at 4.1, 9.7, 10.2, 11.2 and 15.6 degrees two theta±0.2 degrees two theta±0.2 degrees two theta and also having any one, two or three additional peaks selected from PXRD peaks at: 7.8, 14.1 and 18.7±0.2 degrees two theta.

13. The crystalline Form Z of claim 11, wherein said crystalline Form Z is an acetone solvate or an acetonitrile solvate.

14. The crystalline Form Z of claim 11, wherein said crystalline Form Z contains Fidaxomycin with a chemical purity by HPLC of at least 95%, or at least 98%.

15. The crystalline form of Fidaxomycin of claim 1, wherein the crystalline form is Form C characterized by data selected from one or more of the following: a powder X-ray diffraction pattern having peaks at: 6.8, 7.9, 10.0, 10.2, 12.2, 13.4, 14.6, 15.4, 16.4, 17.5, 18.4 and 23.1 degrees two theta±0.1 degrees two theta; a powder X-ray diffraction pattern substantially as depicted in FIG. 7; and by combinations of these data.

16. The crystalline Form C of claim 15, wherein said crystalline Form C contains Fidaxomycin with a chemical purity by HPLC of >98%, >99% or >99.3%.

17. The crystalline Form C of claim 15, wherein said crystalline Form C is obtainable by a process comprising:
  a) providing a solution of Fidaxomycin having a chemical purity of >95%, or >98% by HPLC in methanol;
  b) heating said solution to a temperature of about 55° C. to about 60° C.;
  c) adding water to the heated solution;
  d) maintaining the temperature of the heated solution at about 55° C. to about 60° C. for a period of about an hour;
  e) cooling the heated solution to a temperature of about 15° C. to obtain a suspension comprising the crystalline Form C; and
  f) optionally maintaining the suspension at about 15° C. for a period of about 2 hours.

18. Crystalline Fidaxomycin solvate, wherein the solvate is acetone solvate or acetonitrile solvate.

19. A pharmaceutical composition comprising one or more crystalline forms of Fidaxomycin of claim 1.

20. A pharmaceutical formulation comprising the pharmaceutical composition according to claim 19, and at least one pharmaceutically acceptable excipient.

21. A process for preparing a pharmaceutical formulation comprising combining one or more crystalline forms of Fidaxomycin of claim 1 and at least one pharmaceutically acceptable excipient.

22. A method of treating a person suffering from *Clostridium difficile* infection or *Clostridium difficile*-associated disease, comprising administering a therapeutically effective amount of one or more of the crystalline forms of Fidaxomycin of claim 1.

23. A method of treating a person suffering from *Clostridium difficile* infection or *Clostridium* or *Clostridium difficile*-associated disease, comprising administering a therapeutically effective amount of the pharmaceutical formulation of claim 20.

* * * * *